US011274966B2

(12) United States Patent
Jang et al.

(10) Patent No.: US 11,274,966 B2
(45) Date of Patent: Mar. 15, 2022

(54) HYPER-SPECTRAL IMAGE MEASUREMENT DEVICE AND CALIBRATION METHOD THEREFOR, PHOTOGRAPHING MODULE AND DEVICE FOR SKIN DIAGNOSIS, SKIN DIAGNOSIS METHOD, AND SKIN IMAGE PROCESSING METHOD

(71) Applicant: SEOUL VIOSYS CO., LTD.

(72) Inventors: Seong Tae Jang, Ansan-si (KR); Stella Park, Ansan-si (KR); Sung Il Park, Ansan-si (KR); Ji Ye Song, Ansan-si (KR); Woong Ki Jeong, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 0 days.

(21) Appl. No.: 16/780,638

(22) Filed: Feb. 3, 2020

(65) Prior Publication Data
US 2020/0182698 A1 Jun. 11, 2020

Related U.S. Application Data

(63) Continuation of application No. 15/842,770, filed on Dec. 14, 2017, now Pat. No. 10,551,248, which is a (Continued)

(51) Int. Cl.
*G01J 3/42* (2006.01)
*G02B 7/02* (2021.01)
(Continued)

(52) U.S. Cl.
CPC ............... *G01J 3/42* (2013.01); *A61B 5/0075* (2013.01); *A61B 5/441* (2013.01); *A61B 5/6898* (2013.01);
(Continued)

(58) Field of Classification Search
CPC .. G01J 3/42; G01J 3/0256; G01J 3/027; G01J 3/0291; G01J 3/0297; G01J 3/01;
(Continued)

(56) References Cited

U.S. PATENT DOCUMENTS 6,011,648 A * 1/2000 Mukai ............... G02B 15/1435
359/431
6,096,846 A 8/2000 Oda et al.
(Continued)

FOREIGN PATENT DOCUMENTS

KR 10-2004-0004216 A 1/2004
KR 10-0781235 B1 11/2007
(Continued)

OTHER PUBLICATIONS

International Search Report in International Application No. PCT/KR2016/005449, dated Aug. 23, 2016.
(Continued)

*Primary Examiner* — Jamil Ahmed
(74) *Attorney, Agent, or Firm* — Perkins Coie LLP

(57) ABSTRACT

In one aspect, a hyperspectral image measurement device is provided to include: a main body; an illumination module disposed in the main body and including LEDs having different peak wavelengths to irradiate light to a subject; a camera disposed on the main body and receiving light reflected from the subject to acquire an image of the subject; a barrel having a contact surface contacting the subject, the contact surface located to be spaced apart from the illumination module and the camera module by a predetermined distance; and a reference cover located on the contact surface and including a standard reflection layer for reflecting light irradiated from the illumination module toward the camera module.

12 Claims, 24 Drawing Sheets

Related U.S. Application Data continuation of application No. PCT/KR2016/005449, filed on May 23, 2016.

(51) Int. Cl.

| | | |
|---|---|---|
| *A61B 5/00* | (2006.01) | |
| *G01N 21/31* | (2006.01) | |
| *G01J 3/28* | (2006.01) | |
| *G01J 3/02* | (2006.01) | |
| *G01J 3/10* | (2006.01) | |
| *G02B 6/12* | (2006.01) | |
| *G01N 21/64* | (2006.01) | |
| *G01N 21/27* | (2006.01) | |

(52) U.S. Cl.
CPC ............ *G01J 3/027* (2013.01); *G01J 3/0256* (2013.01); *G01J 3/0291* (2013.01); *G01J 3/0297* (2013.01); *G01J 3/10* (2013.01); *G01J 3/2803* (2013.01); *G01J 3/2823* (2013.01); *G01N 21/31* (2013.01); *G02B 6/12* (2013.01); *G02B 7/02* (2013.01); *G01J 2003/104* (2013.01); *G01J 2003/106* (2013.01); *G01J 2003/2859* (2013.01); *G01J 2003/2866* (2013.01); *G01J 2003/425* (2013.01); *G01N 21/278* (2013.01); *G01N 21/6456* (2013.01); *G01N 21/6486* (2013.01); *G01N 2021/3181* (2013.01); *G01N 2201/0221* (2013.01); *G01N 2201/0627* (2013.01); *G02B 2006/12083* (2013.01)

(58) Field of Classification Search
CPC .. G01J 3/2803; G01J 3/2823; G01J 2003/104; G01J 2003/106; G01J 2003/2859; G01J 2003/2866; G01J 2003/425; A61B 5/0075; A61B 5/441; A61B 5/6898; G01N 21/31; G01N 21/278; G01N 21/6456; G01N 21/6486; G01N 2021/3181; G01N 2201/0221; G01N 2201/0627; G02B 6/12; G02B 7/02; G02B 2006/12083

See application file for complete search history.

(56) References Cited

U.S. PATENT DOCUMENTS

| | | |
|---|---|---|
| 2002/0138008 A1* | 9/2002 | Tsujita ................... A61B 1/05 600/473 |
| 2006/0274431 A1 | 12/2006 | Wood |
| 2008/0147053 A1 | 6/2008 | Kang et al. |
| 2013/0096392 A1 | 4/2013 | Adams |
| 2018/0106676 A1 | 4/2018 | Seong et al. |

FOREIGN PATENT DOCUMENTS

| | | |
|---|---|---|
| KR | 10-2008-0056034 A | 6/2008 |
| KR | 10-2012-0140328 A | 12/2012 |
| KR | 10-2014-0004469 A | 1/2014 |
| KR | 10-2014-0096262 A | 8/2014 |
| KR | 10-1425203 B1 | 8/2014 |
| KR | 10-2015-0094196 A | 8/2015 |
| WO | 2008062967 A1 | 5/2008 |

OTHER PUBLICATIONS

English translation of Korean Office Action from related Korean patent application No. 10-2015-0083989 dated Jan. 22, 2021 (5 pages).

English translation of Korean Office Action from related Korean patent application No. 10-2015-0136542 dated Oct. 20, 2021 (6 pages).

\* cited by examiner

HYPER-SPECTRAL IMAGE MEASUREMENT DEVICE AND CALIBRATION METHOD THEREFOR, PHOTOGRAPHING MODULE AND DEVICE FOR SKIN DIAGNOSIS, SKIN DIAGNOSIS METHOD, AND SKIN IMAGE PROCESSING METHOD

CROSS-REFERENCE TO RELATED APPLICATIONS

This application is a continuation of U.S. application Ser. No. 15/842,770, filed on Dec. 14, 2017 and claims the benefit of International Application No. PCT/KR2016/005449, filed on May 23, 2016, which claims further priority to Korean Patent Application No. 10-2015-0083989, filed Jun. 15, 2015, Korean Patent Application No. 10-2015-0136542, dated Sep. 25, 2015, Korean Patent Application No. 10-2015-0136543, filed Sep. 25, 2015, Korean Patent Application No. 10-2015-0136544, filed Sep. 25, 2015, and Korean Patent Application No. 10-2015-0137264, filed Sep. 30, 2015. The entire contents of the before-mentioned patent applications are incorporated by reference as part of the disclosure of this application.

BACKGROUND

Technical Field

The present disclosure relates to a hyperspectral image measurement device and a calibration method thereof, a camera module and a device for diagnosing skin, a method for diagnosing skin, and a skin image processing method.

Discussion of the Background

A hyperspectral image may be defined as a material that can obtain a complete spectral reflectance curve of an object corresponding to each pixel constructing an image. The hyperspectral image is an image that may be defined as three features of many spectral bands, a continuous bandwidth, and a narrow bandwidth.

Unlike the conventional spectrometer, the hyperspectral image may obtain the spectral reflectance curve for all pixels constructing an image, and extract information associated with a target corresponding to each pixel using the spectral reflectance curve.

The hyperspectral measurement device used to obtain the above-described hyperspectral image is a device for obtaining an image under different monochromatic illumination, and is a device equipped with various kinds of monochromatic illumination and camera.

SUMMARY

Exemplary embodiments of the present disclosure provide a hyperspectral image measurement device and a calibration method thereof capable of providing a calibration method and a tool for converting an image acquired using a hyperspectral measurement device into a reflectance map.

Exemplary embodiments of the present disclosure provide a camera module and a device for skin diagnosis capable of being used by replacing only necessary parts in accordance with a skin disease to be diagnosed.

Exemplary embodiments of the present disclosure provides a camera module and a device for skin diagnosis which enables anyone to diagnose skin personally at home without any difficulty.

Exemplary embodiments of the present disclosure provide a skin camera module capable of photographing each image at the same scale when a plurality of connected places of skin are enlarged and photographed and minimizing occurrence of errors when a plurality of enlarged images obtained by enlarging and photographing skin are composed.

Exemplary embodiments of the present disclosure provide a skin image processing method capable of expressing a composed image by easily matching the composed image with actual skin.

Exemplary embodiments of the present disclosure provide a device for diagnosing acne vulgaris capable of effectively treating the acne vulgaris before the acne vulgaris occurs by diagnosing a skin location, where the acne vulgaris is highly likely to occur, in advance before the acne vulgaris occurs as well as the acne vulgaris which has already occurred.

An exemplary embodiment of the present disclosure provides a hyperspectral image measurement device including: a main body; an illumination module installed in the main body and including a plurality of LEDs having different peak wavelengths to irradiate light to a subject; a camera module installed in the main body and measuring light reflected from the subject to acquire an image of the subject; a barrel provided with a contact surface contacting the subject and installed in the main body so that the contact surface is located to be spaced apart from the illumination module and the camera module by a predetermined distance; and a reference cover installed on the barrel to be located on the contact surface and including a standard reflection layer for reflecting light irradiated from the illumination module toward the camera module.

The standard reflection layer may be formed by coating an inner side surface of the reference cover with a substance having known reflectance for each wavelength.

The reference cover may be detachably installed on the barrel.

The barrel may be installed on the main body so that a closed space is formed between the contact surface and the illumination module and the camera module.

The barrel may be detachably installed on the main body.

The main body may include a display for displaying the acquired image.

The main body may be connected to a mobile device so that the acquired image is displayed on a display of the mobile device.

The main body may be the mobile device, and the illumination module and the barrel are formed as one combined body to be detachably installed on the main body.

The combined body may further include the camera module.

The illumination module may include a plurality of LEDs having different peak wavelengths.

An exemplary embodiment of the present disclosure provides a calibration method of a hyperspectral image measurement device including: acquiring a reference intensity map by photographing light reflected from a standard reflection layer; acquiring a target intensity map by photographing light reflected from a substance or a biological tissue surface to be measured; and acquiring a reflectance map based on the acquired reference intensity map and target intensity map.

The acquiring of the reference intensity map may include: installing the reference cover so that the standard reflection layer is located on the contact surface of the barrel installed on the main body; irradiating light toward the standard reflection layer by turning on the LED included in the illumination module; and measuring the light reflected from the standard reflection layer.

The combined body may further include the camera module.

The standard reflection layer may be formed by coating an inner side surface of the reference cover with a substance having known reflectance for each wavelength.

The combined body may further include the camera module.

The acquiring of the target intensity map may include: removing the reference cover installed on the barrel; locating the substance or the biological tissue surface to be measured on the contact surface; irradiating light toward the substance or the biological tissue surface to be measured by turning on the LED included in the illumination module; and measuring the light reflected from the substance or the biological tissue surface to be measured.

In the acquiring of the reflectance map, a reflectance value for acquiring the reflectance map may be acquired by using values obtained by dividing numerical values of intensities of light for each wavelength included in the target intensity map by numerical values of intensities of light for each wavelength included in the reference intensity map.

An exemplary embodiment of the present disclosure provides a device for diagnosing skin including: a camera module that includes a housing whose tip part contacts the skin, a substrate installed in the housing, and an LED mounted on the substrate to irradiate light in a first wavelength band toward the skin contacting the tip part; a base fixed to a portable terminal; and a first detachable opening detachably fastened with the camera module.

The camera module may further include a lens that is installed in the housing and located on a path through which light emitted from the skin is incident on an image sensor to adjust a focal distance of the skin, which contacts the tip part of the housing, to the image sensor.

The camera module may further include a long pass filter that is installed in the housing and located on the path through which the light emitted from the skin is incident on the image sensor to block the light in the first wavelength band which is a wavelength irradiated from the LED and transmit light in a second wavelength band having a longer wavelength than that of the light in the first wavelength band.

The lens may have a function of a long pass filter that blocks the light in the first wavelength band which is the wavelength irradiated from the LED and transmits light in a second wavelength band having a longer wavelength than that of the light in the first wavelength band.

The lens may be made of PMMA and may be manufactured in a state in which the PMMA is mixed with a pigment absorbing the light in the first wavelength band.

The substrate may be provided with a hole, the hole may be disposed on a central axis in a longitudinal direction of the housing within the housing, and the LED may be mounted around the hole and radially disposed at regular intervals with respect to the central axis in the longitudinal direction of the housing.

The substrate may be provided with the hole, the hole may be disposed on the central axis in the longitudinal direction of the housing within the housing, the lens may be disposed to be closer to the image sensor than the substrate, and a center of the lens may be aligned at the central axis in a longitudinal direction of the housing.

The substrate may be provided with the hole, the hole may be disposed on the central axis in the longitudinal direction of the housing within the housing, and the long pass filter may be disposed to be closer to the image sensor than the substrate.

The substrate may be provided with the hole, the hole may be disposed on the central axis in the longitudinal direction of the housing within the housing, and the housing may include a large barrel portion whose tip part contacts the skin, a small barrel part having a diameter relatively smaller than that of the large barrel portion, and an annular stepped portion connecting between end parts at which the large barrel portion faces the small barrel portion, in which the substrate may be housed in the large barrel portion and installed in parallel with the stepped portion.

A base end part of the housing may be provided with a second detachable opening that is detachably fastened with the first detachable opening.

The first detachable opening and the second detachable opening may be fastened with each other in a female screw manner and a male screw manner.

The first detachable opening and the second detachable opening may be two magnets that act as attraction to each other.

The first detachable opening and the second detachable opening may be fitting parts that are tightly fitted in each other.

The first detachable opening may be separably fixed to the base, and the first detachable opening may include a detachable portion that is detachably fastened with the camera module and a base fixing portion that is separably fixed to the base.

The base may be a case of the portable terminal.

The base may be the case of the portable terminal, the case may be provided with a through hole so that an optical lens and an image sensor portion of the portable terminal are aligned, and the first detachable opening may be fitted from a back face of the case toward the through hole, and the base fixing portion may have a diameter larger than that of the through hole of the case.

The camera module may further include a battery that is housed in the housing, charged by being supplied with power from an outside, and discharged to supply power to the LED.

The substrate may be provided with a switch that controls a turn on/off of the camera module.

The substrate may be provided with a module that provides near field communication with the portable terminal.

The device for diagnosing skin may further include the portable terminal fixed to the base, and the image sensor of the portable terminal may include a blue light sensing element, a green light sensing element, and a red light sensing element.

The device for diagnosing skin may further include the portable terminal fixed to the base, and the portable terminal may be provided with a program that controls the diagnosis module and processes the image photographed by the image sensor.

The program may generate a signal for informing that a skin condition is abnormal as a result of image processing.

The program may display the photographed image on the display of the portable terminal.

An exemplary embodiment of the present disclosure provides a skin photographing and image processing device including: a barrel whose tip part contacts the skin; a substrate installed in the barrel; an LED mounted on the substrate to irradiate light in a first wavelength band toward the skin contacting the tip part; an image sensor photographing the skin contacting the tip part of the barrel; and a central processing unit composing images photographed adjacent to at least other one image as a plurality of images photographed by the image sensor.

The skin photographing and image processing device may further include a lens that is installed in the barrel and located on a path through which light emitted from the skin is incident on an image sensor to adjust a focal distance of the skin, which contacts the tip part of the barrel, to the image sensor.

The skin photographing and image processing device may further include a long pass filter that is installed in the barrel and located on the path through which the light emitted from the skin is incident on the image sensor to block the light in the first wavelength band which is a wavelength irradiated from the LED and transmit light in a second wavelength band having a longer wavelength than that of the light in the first wavelength band.

The lens may have a function of a long pass filter that blocks the light in the first wavelength band which is the wavelength irradiated from the LED and transmits light in a second wavelength band having a longer wavelength than that of the light in the first wavelength band.

The lens may be made of PMMA and may be manufactured in a state in which the PMMA is mixed with a pigment absorbing the light in the first wavelength band.

The substrate may be provided with a hole, the hole may be disposed on a central axis in a longitudinal direction of the barrel within the barrel, and the LED may be mounted around the hole and radially disposed at regular intervals with respect to the central axis in the longitudinal direction of the barrel.

The substrate may be provided with the hole, the hole may be disposed on the central axis in a longitudinal direction of the barrel within the barrel, the lens may be disposed to be closer to the image sensor than the substrate, and a center of the lens may be aligned at the central axis in a longitudinal direction of the barrel.

The substrate may be provided with the hole, the hole may be disposed on the central axis in the longitudinal direction of the barrel within the barrel, and the long pass filter may be disposed to be closer to the image sensor than the substrate.

The image sensor and the central processing unit may be built in a portable terminal, the barrel, the substrate, and the LED may be a camera module and detachably coupled to the portable terminal, and the image composition may be performed by an application installed in the portable terminal.

The photographed images may be composed based on a shape and an arrangement of wrinkles and pores on the skin.

The skin photographing and image processing device may further include a marker displayed on the skin.

An exemplary embodiment of the present disclosure provides a skin photographing and image processing device including: a marker displayed on skin; an LED mounted on the substrate to irradiate light in a first wavelength band toward the skin; an image sensor photographing the skin; and a central processing unit composing images photographed adjacent to at least one other image as a plurality of images photographed by the image sensor.

The photographed images may be composed based on the marker displayed on the skin along with a shape and an arrangement of wrinkles and pores on the skin.

The marker may be displayed at two different points on the skin, and at least any one of a size, a shape, and a color of the markers displayed at the two points may be different from each other.

The marker may be displayed at two different points on the skin, and each marker displayed at the two points may have a shape to distinguish directivity.

An exemplary embodiment of the present disclosure provides a skin photographing and image processing method including: displaying a marker on the skin; dividing a region of the skin including the marker into a plurality of photographing regions adjacent to each other and photographing the divided regions; and composing the photographed images.

The marker may be displayed at two different points on the skin, and at least any one of a size, a shape, and a color of the markers displayed at the two points may be different from each other.

The marker may be displayed at two different points on the skin, and each marker displayed at the two points may have a shape to distinguish directivity.

The photographing may be performed in a state in which the tip part of the barrel contacts the skin, and the barrel is provided with the LED that irradiates the light in the first wavelength band toward the tip part so that light other than the light in the first wavelength band is not irradiated to the skin.

The light removed by filtering the light in the first wavelength band may be photographed when the skin is photographed.

The photographed images may be composed based on the marker displayed on at least skin.

An exemplary embodiment of the present disclosure provides a diagnosis module including: a housing including a barrel whose tip part contacts skin; a substrate installed in the housing; an LED mounted on the substrate and located in a space in the barrel when the substrate is installed in the housing; and a lens that is installed in the barrel and located on a path through which light emitted from the skin is incident on an image sensor to adjust a focal distance of the skin, which contacts the tip part of the barrel, to the image sensor.

The diagnosis module may further include a long pass filter that is installed in the barrel and located on the path through which the light emitted from the skin is incident on the image sensor to block the light in the first wavelength band which is a wavelength irradiated from the LED and transmit light in a second wavelength band having a longer wavelength than that of the light in the first wavelength band.

The lens may have a function of a long pass filter that blocks the light in the first wavelength band which is the wavelength irradiated from the LED and transmits light in a second wavelength band having a longer wavelength than that of the light in the first wavelength band.

The lens may be made of PMMA and may be manufactured in a state in which the PMMA is mixed with a pigment absorbing the light in the first wavelength band.

The substrate may be provided with a hole, the hole may be disposed on a central axis in a longitudinal direction of the barrel within the barrel, and the LED may be mounted around the hole and radially disposed at regular intervals with respect to the central axis in the longitudinal direction of the barrel.

The lens may be installed in the barrel while being fixed to the lens mounter, and provide a fixing force fixing the substrate to the housing while the lens mounter being fixed to the barrel.

The lens and the pass filter may be installed in the barrel while being fixed to the lens mounter, and provide a fixing force fixing the substrate to the housing while the lens mounter being fixed to the barrel.

The diagnosis module may further include a battery that is housed in the housing, charged by being supplied with power from an outside, and discharged to supply power to the LED.

The substrate may be provided with a switch that controls a turn on/off of the diagnosis module.

The substrate may be provided with a Bluetooth module that provides near field communication with the portable terminal including the image sensor.

The substrate may be provided with a charging terminal.

The peak wavelength of the light in the first wavelength band irradiated from the LED may range from 380 nm and 420 nm.

The light in the second wavelength band may include light of 520 nm and in the vicinity thereof.

The present disclosure provides the diagnosis module and the device for diagnosing skin including the portable terminal that is fastened with the diagnosis module and has the image sensor built therein.

When the diagnosis module is fastened with the portable terminal, the image sensor and the barrel may be guided to each other so that the image sensor is aligned with the barrel.

The image sensor may include a blue light sensing element, a green light sensing element, and a red light sensing element.

The portable terminal may be provided with a program that controls the diagnosis module and processes the image photographed by the image sensor.

The program may generate a signal for informing that a skin condition is abnormal as a result of image processing.

The program may display the photographed image on the display of the portable terminal.

When a location where the skin condition is abnormal is determined as an image processing result, the program may display the location on the display.

The program may control the LED of the diagnosis module to perform the PDT when the skin condition is abnormal as the image processing result.

An exemplary embodiment of the present disclosure provides a method for diagnosing skin using light in a first wavelength band and light in a second wavelength band having a wavelength longer than that of the light in the first wavelength band, the method including: irradiating the light in the first wavelength band to the skin to be diagnosed without the light in the second wavelength band being irradiated thereto; performing filtering to block the light in the first wavelength band emitted from the skin and transmit the light in the at least second wavelength band; photographing the filtered light by an image sensor; diagnosing the skin by performing an image process based on optical information of the at least second wavelength band among information on the photographed image.

The light in the first wavelength band may include a wavelength at which a predetermined substance in the skin has a high absorption rate, and the light in the second wavelength band may include at least a part of the wavelength at which the predetermined substance fluoresces.

The peak wavelength of the light in the first wavelength band may range from 380 nm and 420 nm.

The light in the second wavelength band may include light of 520 nm and in the vicinity thereof.

The image sensor may include a blue light sensing element, a green light sensing element, and a red light sensing element.

The image process may include a process of calculating the optical information of the second wavelength band for each pixel in the photographed image.

The image process may extract RGB values for each pixel from an output value of the blue light sensing element, an output value of the green light sensing element, and an output value of the red light sensing element, and calculate the optical information of the second wavelength band of the corresponding pixel based on the RBG values.

The case in which the calculated optical information of the second wavelength band is higher than a threshold value may be considered as a requirement of a skin condition determination.

The case in which an area in which pixels in which the calculated optical information of the second wavelength band is higher than a reference value may be distributed while contacting each other is equal to or more than a reference area may be considered as the requirement of the skin condition determination.

The method may further include displaying the photographed image on the display.

The method may further include displaying a part in which the skin condition is determined on the photographed image.

The method may further include generating a signal informing the fact that the part in which the skin condition is determined is equal to or more than a predetermined ratio with respect to the area of the photographed image.

The light in the first wavelength band may be irradiated using the LED.

The method may further include performing photodynamic therapy (PDT) that irradiates the light in the first wavelength band to the skin using the LED.

An irradiated amount of the light in the first wavelength band may be further increased when the light in the first wavelength band is irradiated to the skin to be diagnosed for the PDT than when the light in the first wavelength band is irradiated to the skin.

At least any one of a control to increase the number of turned-on LEDs and a control to increase power supplied to the LED may be performed to further increase the irradiated amount of light.

The image sensor may be installed in the portable terminal.

DETAILED DESCRIPTION OF THE EMBODIMENTS

Figure 1:
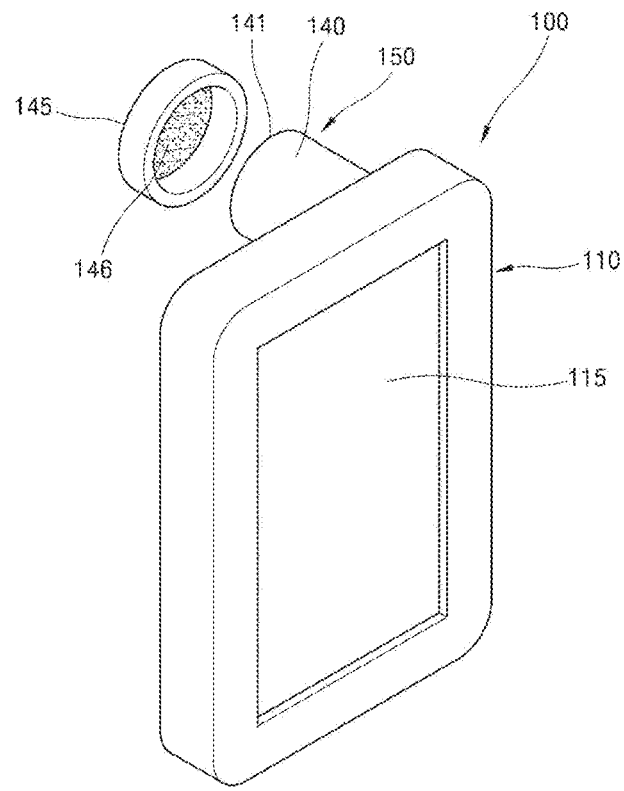
FIG. 1 is a perspective view of an exemplary hyperspectral image measurement device according to an embodiment of the present disclosure.

Hereinafter, a hyperspectral image measurement device and a calibration method thereof according to an embodiment of the present disclosure will be described with reference to the accompanying drawings. For convenience of explanation, a thickness of lines, a size of components, or the like, illustrated in the drawings may be exaggeratedly illustrated for clearness and convenience of explanation.

An LED may be used as the monochromatic illumination provided in the hyperspectral measurement device. Since reflection characteristics of each single wavelength LED provided in the hyperspectral measurement device may vary depending on a use period, a use frequency, etc., to obtain a reflectance map having a physical meaning and high accuracy, there is a need for calibration for converting the image, which is acquired by using the hyperspectral measurement device, into the reflectance map.

However, since there is no calibration method and tool for converting an image which is acquired by using the hyperspectral measurement device into a reflectance map as described above, it is difficult to obtain the reflectance map having the physical meaning and high accuracy.

Meanwhile, skin in the human body is an element confronting the outside environment, and includes various metabolites and constituents, and is often an indicator that indicates a health status.

Accordingly, there is a demand for a device and method for diagnosing a skin condition capable of performing monitoring and diagnosis more conveniently without causing discomfort to a person to be diagnosed.

However, since the devices for diagnosing skin by irradiating light and photographing skin are mostly configured of bulky, expensive equipment, the devices are mainly used in places specializing in skin such as a skin care shop or a dermatology hospital.

On the other hand, an example of obtaining the greatest preventive effect when a process and a criterion for skin diagnosis are established by an optical information analysis method may include acne vulgaris which is one of skin diseases. Accordingly, there is a need for a device capable of simply diagnosing locations where the acne vulgaris is highly likely to occur even at places other than a hospital or a specialized skin care shop as well as diagnosing skin locations, where the acne vulgaris is highly likely to occur, in advance in a contactless manner.

On the other hand, the image required for diagnosing the skin condition is an image obtained by enlarging and photographing the skin as large as possible. By the way, if the skin is enlarged and photographed, only a narrow area of skin may be inevitably photographed. Therefore, for example, when it is desired to diagnose the entire face, it is necessary to compose a plurality of images obtained by photographing different areas into a single large image. However, since human skin is composed of a curved surface, the process of obtaining images by photographing the skin at the same scale becomes very complicated, and the composed images are highly likely to be distorted from actual skin.

Figure 2:
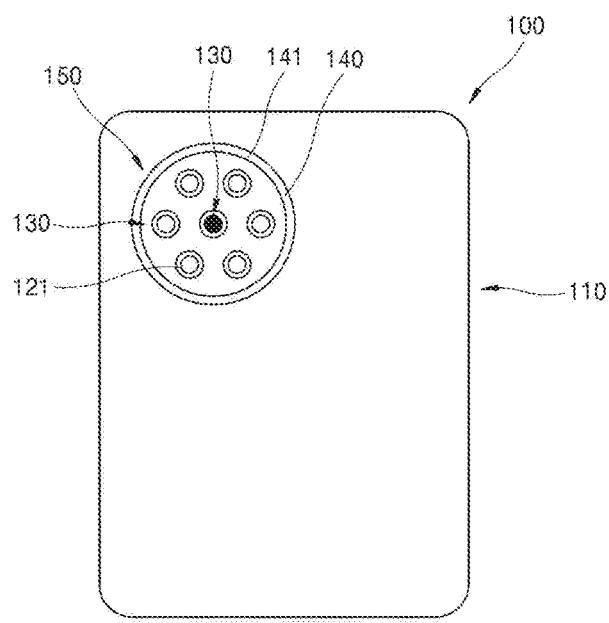
FIG. 2 is a front view showing an exemplary hyperspectral image measurement device according to the embodiment of the present disclosure.
Figure 3:
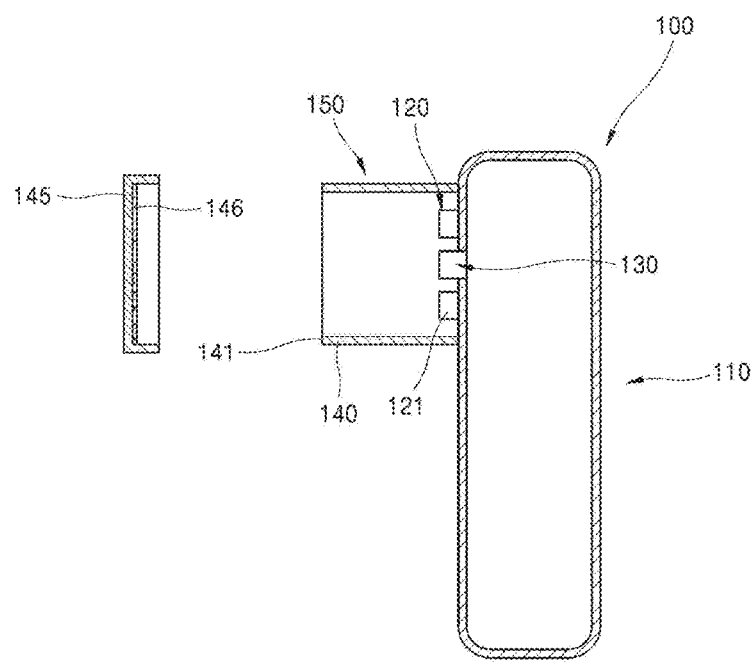
FIG. 3 is a side cross-sectional view of an internal structure of an exemplary hyperspectral image measurement device according to the embodiment of the present disclosure.
Figure 4:
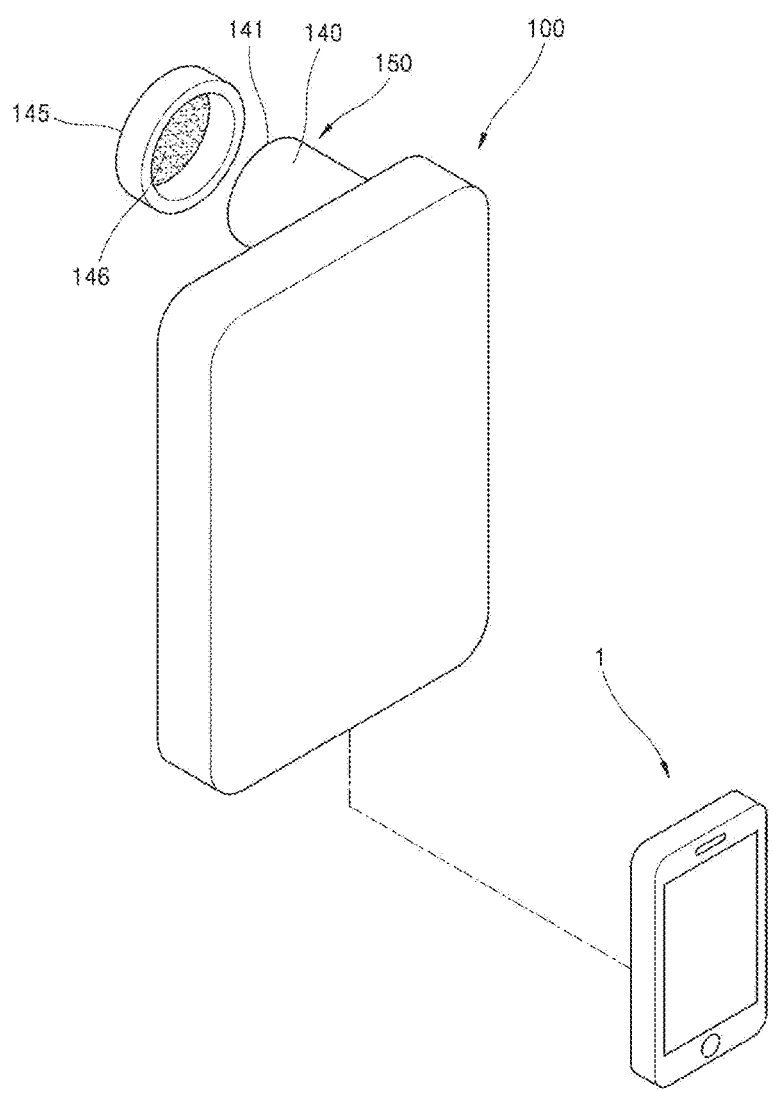
FIG. 4 is a diagram showing an example of a hyperspectral image measurement device.
Figure 5:
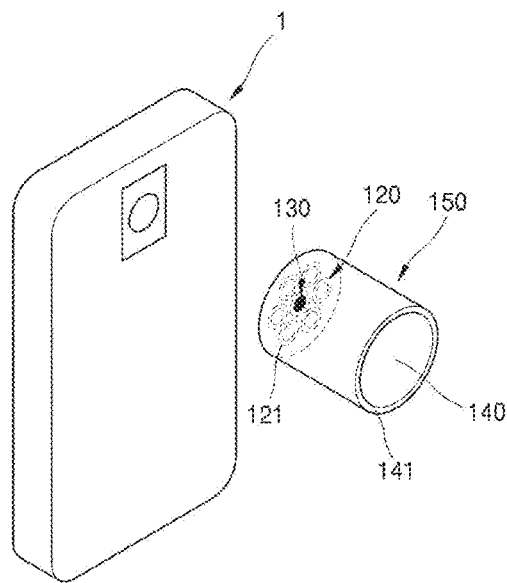
FIG. 5 is a diagram showing another example of the hyperspectral image measurement device.

FIG. 1 is a perspective view of a hyperspectral image measurement device according to an embodiment of the present disclosure, FIG. 2 is a front view showing the hyperspectral image measurement device according to the embodiment of the present disclosure, and FIG. 3 is a side cross-sectional view of an internal structure of the hyperspectral image measurement device according to the embodiment of the present disclosure. FIG. 4 is a diagram showing another example of the hyperspectral image measurement device and FIG. 5 is a diagram showing another example of the hyperspectral image measurement device.

Referring to FIGS. 1 to 3, a hyperspectral image measurement device 100 according to an embodiment of the present disclosure includes a main body 110, an illumination module 120, a camera module 130, a barrel 140, and a reference cover 145.

The main body 110 forms an appearance of the hyperspectral image measurement device 100 according to the present embodiment and various circuits, and devices for operating the illumination module 120 and the camera module 130 are built in the main body 110.

For example, the main body 110 may be provided as a form of an independent separate device, and the main body 110 may include a display 115 which displays the acquired image or provides a screen for operating the illumination module 120 and the camera module 130.

As another example, as shown in FIG. 4, the main body 110 may be provided to be connected to a mobile device 1, such as a smart phone, and the main body 110 may display the acquired image through a display (not shown) which is provided in the mobile device 1.

As another example, as shown in FIG. 5, the main body 110 may be the mobile device 1 such as the smart phone, and the hyperspectral image measurement device 100 may also be provided in a form in which the illumination module 120 (see FIG. 2) and the camera module 130 (see FIG. 2) may be detachably installed on the main body 110 in the form of the mobile device 1 while being formed as a single combined body.

Referring to FIGS. 1 to 3, the illumination module 120 includes a plurality of LEDs 121, which are provided to irradiate light to a subject and have different peak wavelengths.

The illumination module 120 may be installed on the main body 110, and may be installed in the main body 110 in a form where the plurality of LEDs 121 are densely arranged around the camera module 130 to be described later.

The above-described illumination module 120 may be operated in such a manner that each of the plurality of LEDs 121 having different peak wavelengths is sequentially turned on to sequentially irradiate light having different peak wavelengths to each subject.

The camera module 130 measures the light reflected from the subject to acquire an image of the subject.

That is, if the illumination module 120 sequentially turns on the LEDs which illustrate the light having different peak wavelengths, the camera module 130 may photograph a subject every time the turn on of the LED 121 is changed, that is, a color of the light irradiated from the illumination module 120 is changed, thereby acquiring a plurality of images for one subject.

Also, the camera module 130 may acquire a plurality of images by photographing one subject with light of the same color plural times.

The camera module 130 may be provided in a form in which a camera including a device, such as a CCD and a CMOS, is installed on the main body 110 provided in an independent form, and may be provided in a form in which it includes the camera installed on the mobile device 1 (see FIG. 5).

The barrel 140 is detachably installed on the main body 110. The barrel 140 may have a cylindrical shape in which a hollow is formed. One portion of the barrel 140 may be detachably coupled to the main body 110 and the other portion of the barrel 140 may be provided with a contact surface 141.

The barrel 140 thus formed is installed so that the contact surface 141 is located at a predetermined distance from the illumination module 120 and the camera module 130, whereas the barrel 140 is installed on the main body 110 so that a closed space is formed between the contact surface 141 and the illumination module 120 and the camera module 130. At this time, the contact surface 141 may also be formed on another structure other than the barrel 140.

The reference cover 145 includes a standard reflection layer 146 that is provided on the barrel 140 to be located on the contact surface 141 and reflects light irradiated from the illumination module 120 toward the camera module 130.

The reference cover 145 may be detachably installed on the barrel 140 and close the other opened portion of the barrel 140 if being installed on the barrel 140 to be located on the contact surface 141.

The standard reflection layer 146 provided on the reference cover 145 is provided to be located inside the closed barrel 140 when the reference cover 145 is installed on the barrel to be located on the contact surface 141, and an inner side surface of the reference cover 145 may be coated with a substance having known reflectance for each wavelength, for example, a substance such as barium sulfate ($BaSO_4$).

The hyperspectral image measurement device 100 according to the present embodiment configured as described above performs the photographing for the standard reflection layer 146 in a state in which the reference cover 145 is installed on the barrel 140, thereby acquiring a reference intensity map including the information on numerical values of the intensity of light reflected from the surface to be measured for each wavelength.

In addition, the hyperspectral image measurement device 100 according to the present embodiment performs the photographing in a state in which the reference cover 145 is separated from the barrel 140 and a substance or a biological tissue surface (hereinafter, "surface to be measured") to be measured is located on the contact surface 141, thereby acquiring a target intensity map including the information on the numerical values of the intensity of light reflected from the surface to be measured for each wavelength.

The hyperspectral image measurement device 100 according to the present embodiment having the above-described barrel 140 photographs the surface to be measured in the state in which the barrel 140 is separated, thereby acquiring a hyperspectral image for a target to be measured.

As another example, the hyperspectral image measurement device 100 photographs the surface to be measured in the state in which the barrel 140 may be installed, thereby acquiring the hyperspectral image for the target to be measured.

According to the hyperspectral image measurement device 100 as described above, the illumination module 120 and the barrel 140 form a single combined body 150, in which the combined body 150 may be detachably installed on the main body 110.

As another example, the hyperspectral image measurement device 100 may be provided in a form in which the illumination module 120, the camera module 130, and the barrel 140 form the single combined body 150 and the combined body 150 may be detachably installed on the main body 110.

The hyperspectral image measurement device 100 according to the present embodiment having the above-described combined body 150 may be provided in a form in which the combined body 150 is detachably coupled to the main body 110 in an independent separate device type having the display 115, and as shown in FIG. 4, may be provided in a form in which the acquired image is displayed on the display installed on the mobile device 1 by connecting the main body 110 to the mobile device 1 such as a smart phone in a wired or wireless manner.

As another example, as shown in FIG. 5, the hyperspectral image measurement device 100 according to the present embodiment may be provided in a form in which the mobile device 1 such as a smart phone serves as the main body 110 and the combined body 150 configured of the illumination module 120 and the barrel 140 is detachably installed on the mobile device 1.

Figure 6:
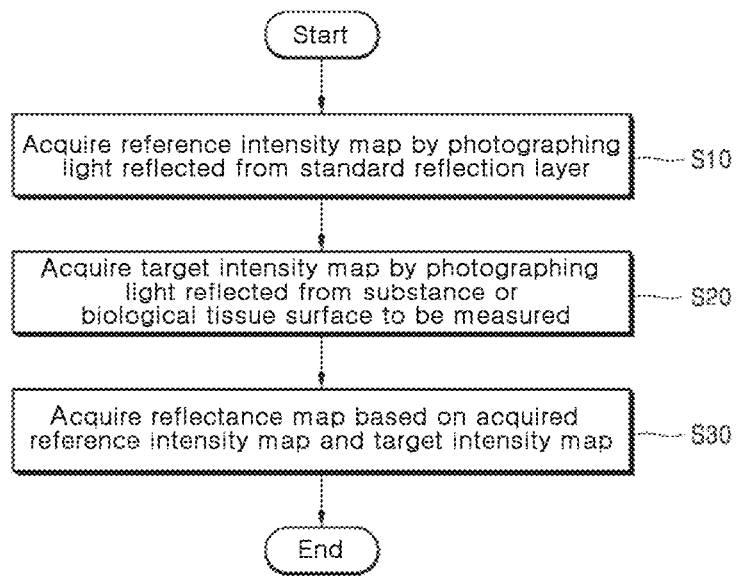
FIG. 6 is a flow chart of a calibration process of an exemplary hyperspectral image measurement device according to an embodiment of the present disclosure.
Figure 7:
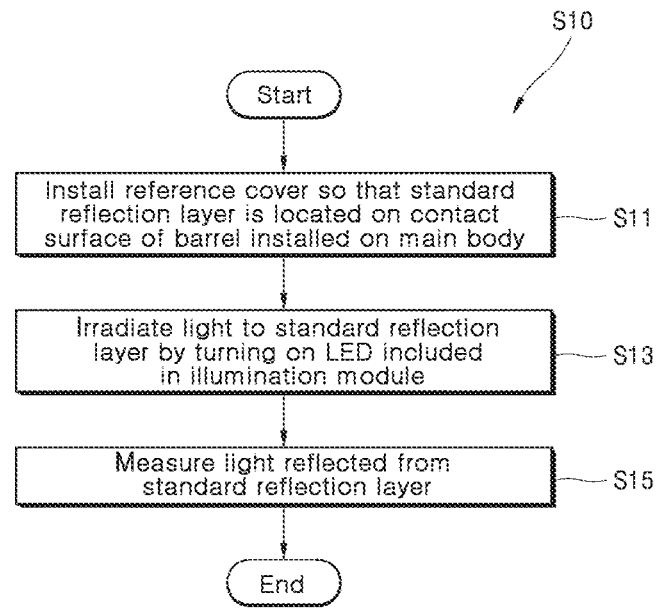
FIG. 7 is a flow chart of an exemplary process of acquiring a reference intensity map.
Figure 8:
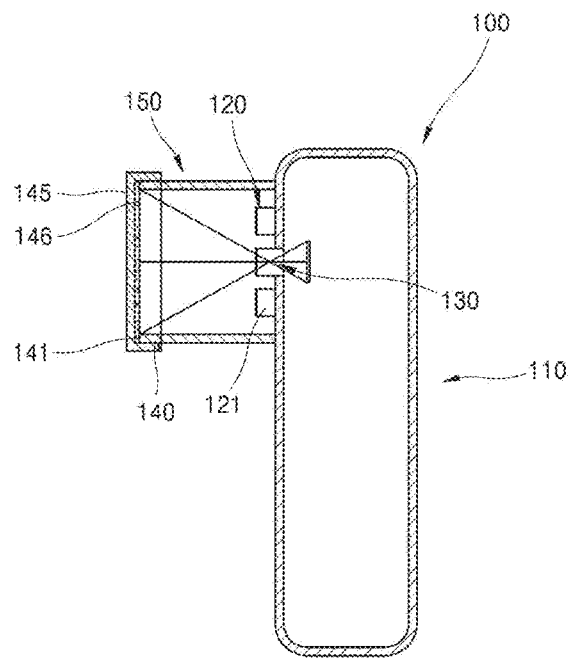
FIG. 8 is a diagram showing a photographing state of an exemplary hyperspectral image measurement device for acquiring a reference intensity map.
Figure 9:
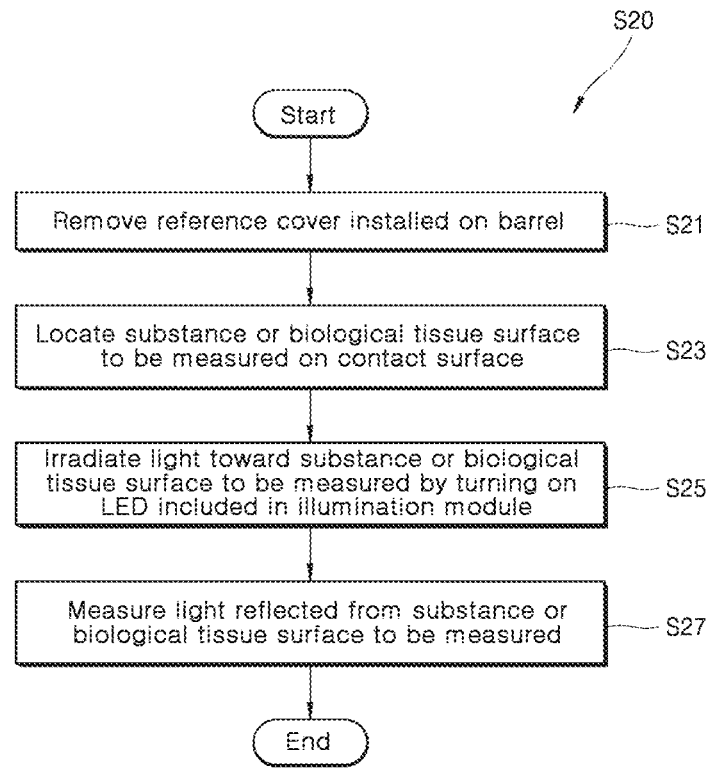
FIG. 9 is a flow chart of an exemplary process of acquiring a target intensity map.
Figure 10:
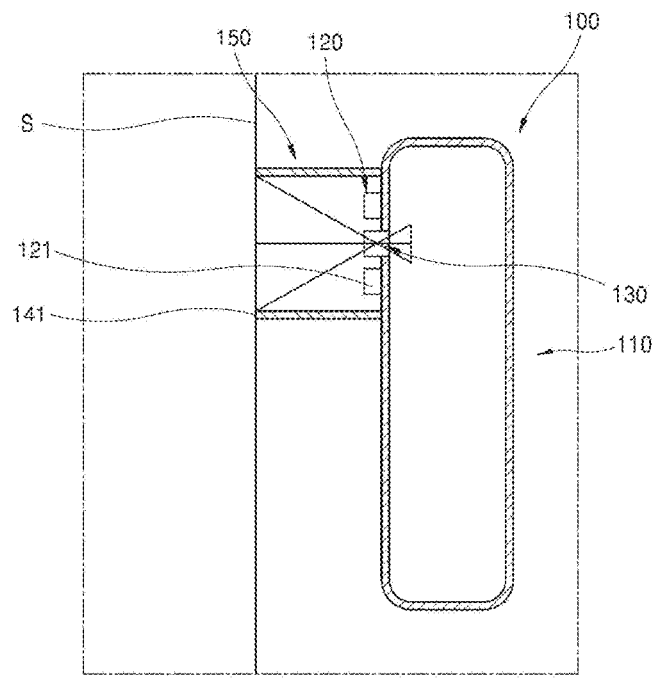
FIG. 10 is a diagram showing a photographing state of an exemplary hyperspectral image measurement device for acquiring a target intensity map.

FIG. 6 is a flow chart of a calibration process of a hyperspectral image measurement device according to an embodiment of the present disclosure, FIG. 7 is a flow chart of a process of acquiring a reference intensity map, and FIG. 8 is a diagram showing a photographing state of a hyperspectral image measurement device for acquiring a reference intensity map. FIG. 9 is a flow chart of a process of acquiring a target intensity map and FIG. 10 is a diagram showing a photographing state of a hyperspectral image measurement device for acquiring a target intensity map.

Hereinafter, the calibration process of the hyperspectral image measurement device according to the present embodiment will be described with reference to FIGS. 2 and 6 to 10.

Referring to FIGS. 2 and 6, for the calibration process of the hyperspectral image measurement device 100 according to the present embodiment, first of all, the reference intensity map is acquired by photographing the light reflected from the standard reflection layer 146 (S10).

The process of acquiring the reference intensity map may be performed as follows.

First of all, as shown in FIGS. 7 and 8, the reference cover 145 is installed so that the contact surface 141 of the barrel 140 which is installed on the main body 110 is provided with the standard reflection layer 146 (S11).

Then, the LED 121 provided in the illumination module 120 is turned on to irradiate light toward the standard reflection layer 146 (S13), and the light reflected from the standard reflection layer 146 is measured (S15).

At this time, the illumination module 120 sequentially turns on the LEDs which irradiate the light having different peak wavelengths and the camera module 130 measures the light reflected from the standard reflection layer 146 every time the light irradiated from the illumination module 120 is changed, such that the reference intensity map including the information on the numerical values of the intensity of light reflected from the standard reflection layer 146 for each wavelength may be acquired.

If the acquisition of the reference intensity map is completed as described above, as shown in FIGS. 2 and 6, the light reflected from the substance or the biological tissue surface to be measured, that is, the surface to be measured is photographed to acquire the target intensity map (S20).

The process of acquiring the target intensity map may be performed as follows.

First of all, as shown in FIGS. 9 and 10, the reference cover 145 (see FIG. 8) provided on the barrel 140 is removed (S21), and a surface S to be measured is located on the contact surface 141 (S23).

Then, the LED 121 provided in the illumination module 120 is turned on to irradiate light toward the surface S to be measured (S25), and the light reflected from the surface S to be measured is measured (S27).

At this time, the illumination module 120 sequentially turns on the LEDs which irradiate the light having different peak wavelengths and the camera module 130 measures the light reflected from the surface S to be measured every time the light irradiated from the illumination module 120 is changed, such that the target intensity map including the information on the numerical values of the intensity of light reflected from the surface to be measured for each wavelength may be acquired.

If the acquisition of the reference intensity map and the target intensity map is completed as described above, as shown in FIGS. 2 and 6, a reflectance map is acquired based on the acquired reference intensity map and target intensity map (S30).

The reflectance map may be acquired in a form in which the numerical value of the reflectance for acquiring the reflectance map is acquired using a value obtained by dividing the information included in the target intensity map, that is, the numerical value of the reflectance on the standard reflection layer 146 by the information included in the reference intensity map, that is, the numerical value of the reflectance on the surface to be measured and the reflectance map is acquired by the acquired numerical value of the reflectance.

That is, if the intensity of light irradiated from the illumination module 120 is I, the intensity of light reflected from the standard reflection layer 146 is $I_R$, and the reflectance at which the light irradiated from the illumination module 120 is reflected from the standard reflection layer 146 is R, the intensity $I_R$ of the light reflected from the standard reflection layer 146 may be expressed by $I_R=I*R$.

In addition, if it is assumed that the intensity of light reflected from the surface to be measured is $I_t$, and the reflectance at which the light irradiated from the illumination module 120 is reflected from the surface to be measured is r, the intensity $I_t$ of light reflected from the surface to be measured may be expressed by $I_t=I*r$.

Accordingly, the reflectance r at which the light irradiated from the illumination module 120 is reflected from the surface to be measured may be expressed by $r=I_t/I$, and if $I_R=I*R$ is substituted thereinto, the reflectance r at which the light irradiated from the illumination module 120 is reflected from the surface to be measured may be summarized by $r=R*I_t/I_R$. At this time, the reflectance R at which the light irradiated from the illumination module 120 is reflected from the standard reflection layer 146 is an already known value, and therefore may be expressed by a constant form.

That is, the reflectance r at which the light irradiated from the illumination module 120 is reflected from the surface to be measured may acquire the numerical value of the reflectance for acquiring the reflectance map using the value ($I_t/I_R$) obtained by dividing the intensity $I_t$ of the light reflected from the surface to be measured by the intensity $I_R$ of the light reflected from the standard reflection layer 146, that is, the value obtained by dividing the numerical value of the intensity of the light for each wavelength included in the target intensity map by the numerical value of the intensity of the light for each wavelength included in the reference intensity map, and the reflectance map may be acquired using the thus acquired numerical value of the reflectance.

It is possible to obtain an accurate reflectance value for the substance or the biological tissue surface to be measured using the thus acquired reflectance map.

According to the hyperspectral image measurement device 100 and the calibration method thereof as described above, it is possible to obtain the reflectance map having the physical meaning and the high accuracy by providing the calibration method and the tool for converting the image acquired by using the hyperspectral measurement device 100 into the reflectance map.

Meanwhile, there are various light absorbing compounds in the human body. Likewise, there are various light absorbing compounds in the skin. The light absorbing compound (chromophore) means a substance which mostly absorbs a specific wavelength in a light spectrum. Meanwhile, each kind of light absorbing compounds has its own unique wavelength band. All biomaterials exhibit a high absorption rate in at least one wavelength range within the wavelength range of light, which is closely related to physical properties of atoms or molecules of a substance. Therefore, so long as the physical properties of atoms or molecules for each biomaterial are different, the wavelength bands of the absorbed light are different from each other.

Figure 11:
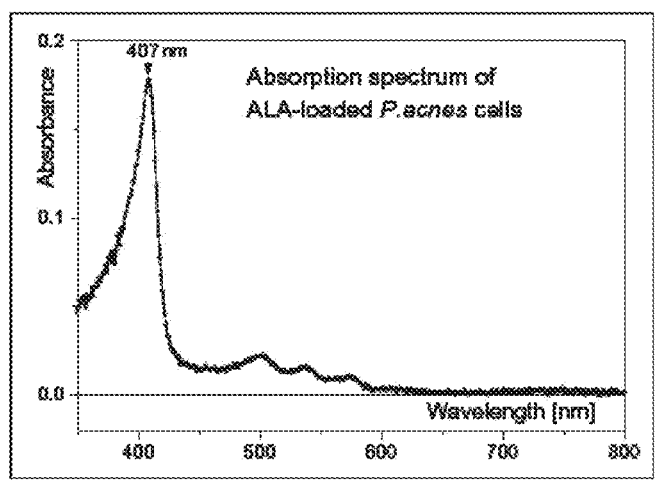
FIG. 11 is an absorption spectrum of copropophyrin 3.

For example, as illustrated in FIG. 11, coproporphyrin 3 which is one of porphyrins generated within skin due to *propionibacterium acne* (*P. acne*) which is bacteria inducing acne vulgaris has an absorption spectrum of 407 nm as a peak.

Meanwhile, autofluorescence refers to a phenomenon that a specific substance absorbs light in a predetermined wavelength band in which a specific substance reacts and emits light in a unique wavelength band having a longer wavelength than that which helps to distinguish biological information medically. There are many specific substances having autofluorescence even in the skin. Therefore, it is possible to grasp how and where any substance is distributed and what the state of the skin is by analyzing the autofluorescence of the skin.

For example, if light in a blue light band (400 to 440 nm) is applied to skin, the porphyrins generated by the *P. acne* among the substances in the skin strongly absorb energy of the light in the blue light band and makes autofluorescence of light in a unique wavelength band different from the absorbed wavelength. As the experiment result, it was confirmed that light in the vicinity of 520 nm and between 600 and 630 nm fluoresces at a hair follicle with sebum where inflammatory reaction is not caused and light in a wavelength band in the vicinity of 520 nm fluoresces at a hair follicle where acne vulgaris, i.e., inflammation is caused or will be caused. Therefore, it is possible to confirm the location, distribution, size, etc. of the part where sebum is simply gathered or the occurrence (possible) part of acne vulgaris by acquiring an autofluorescence image of skin after irradiating blue light of about 407 nm.

Figure 16:
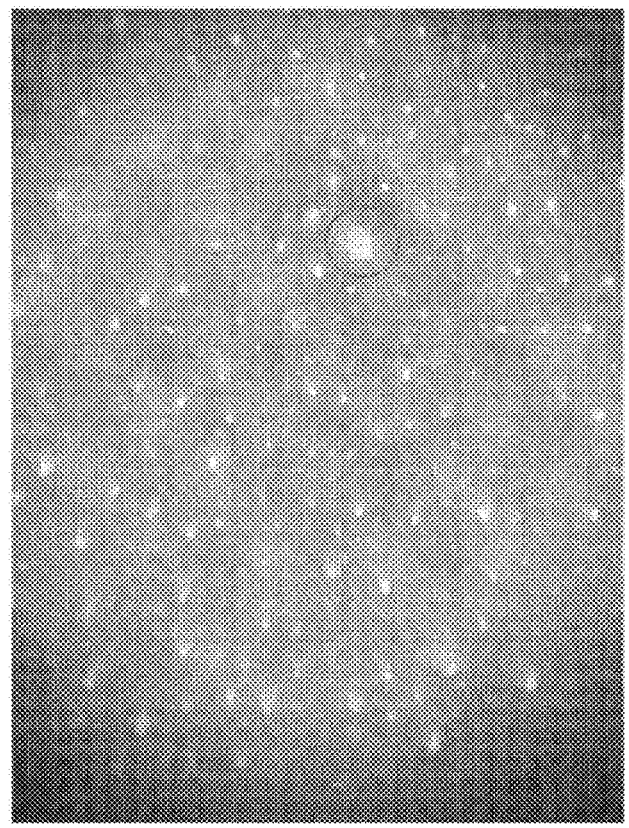
FIG. 16 is a view showing a photographed image displayed after skin goes through a method for diagnosing acne vulgaris.

That is, referring to FIG. 16 showing an image obtained by irradiating light of a first wavelength band to a skin and photographing light which returns from the skin {as will be described later, the light in the first wavelength band is filtered and light in a wavelength band (second wavelength band)} longer than the first wavelength band is provided}, it can be confirmed that light in a wavelength band in the vicinity of 520 nm fluoresces at a hair follicle (circular part shown by a dotted line) where acne vulgaris, i.e., inflammation is caused or will be caused to be a color between green and sky blue.

However, since the photographed image shown in FIG. 16 is the result of enlarging and photographing a skin having a narrow area, it is difficult to match the enlarged and photographed skin with the actually photographed skin.

Figure 12:
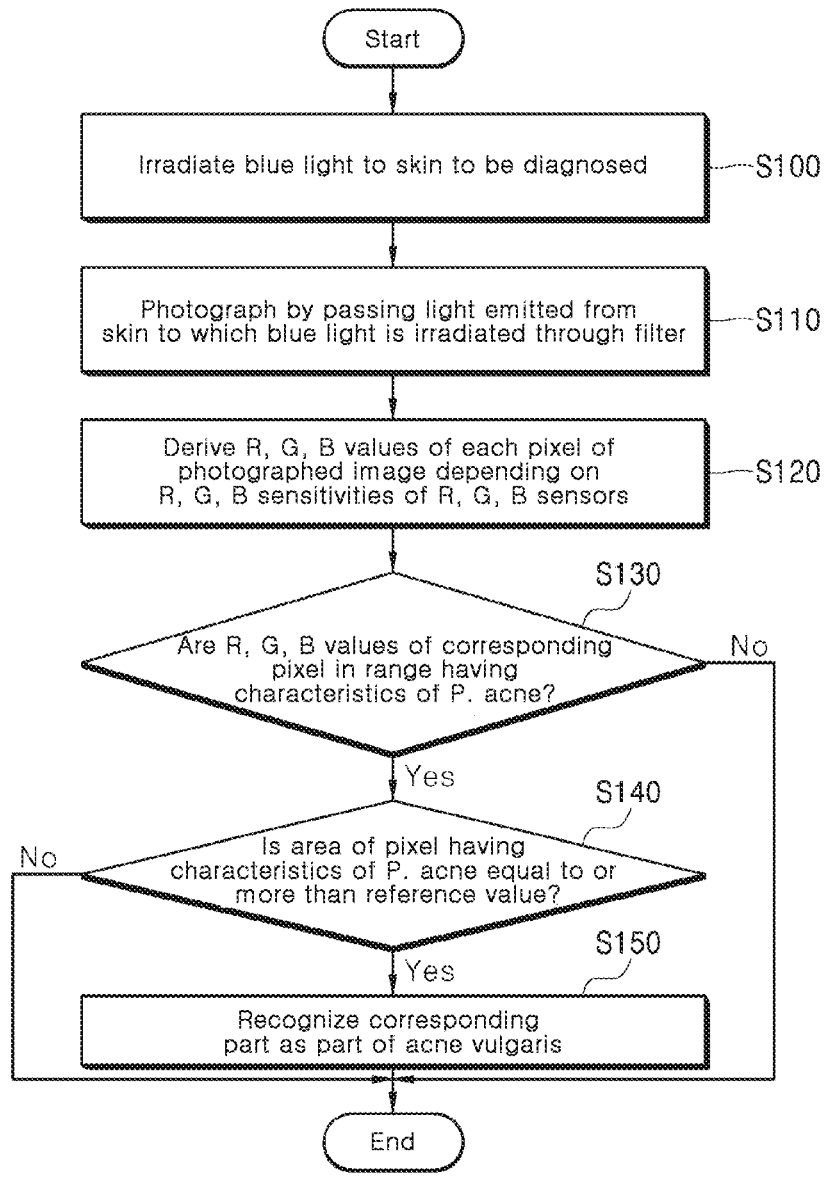
FIG. 12 is a flowchart showing a process of a method for diagnosing acne vulgaris as an example of a method for diagnosing skin according to the present disclosure.

FIG. 12 is a flowchart showing a sequence of the method for diagnosing acne vulgaris as an example of a method for diagnosing skin performed through the camera device for diagnosing skin according to an embodiment of the present disclosure.

Referring to step S100, first of all, light is irradiated to the skin to be diagnosed. As described above, the light irradiated to the skin irradiates the blue light in the first wavelength band having a peak wavelength at 407 nm. In particular, since a light emitting diode (LED) may be produced so that a half width is narrow and a peak wavelength is adjusted to a desired level, if the blue light emitted from the light emitting diode has a peak wavelength at 407 nm and the half width is concentrated near the corresponding peak wavelength, the porphyrin present in the skin may absorb a considerable amount of energy from the blue light. This is true at other wavelength bands as well as at 407 nm which will be used to diagnose acne vulgaris.

Figure 13:
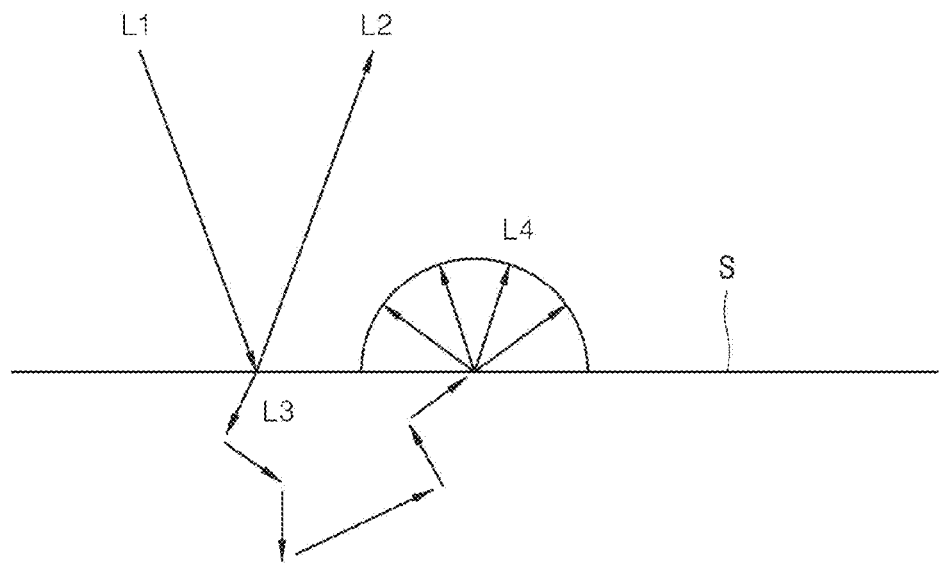
FIG. 13 is a diagram showing various optical paths that are generated after light irradiated to skin reaches the skin.

FIG. 13 is a diagram showing various optical paths that are generated after light irradiated to skin reaches the skin. If the blue light is irradiated to the skin S, some (L2) of the blue light L1 reaching the skin is immediately reflected from the skin surface, and some (L3) thereof penetrates into the skin to some extent. The blue light that penetrates into the skin is repeatedly refracted, absorbed and scattered from the inside, and is scattered out of the skin again (L4).

Figure 14:
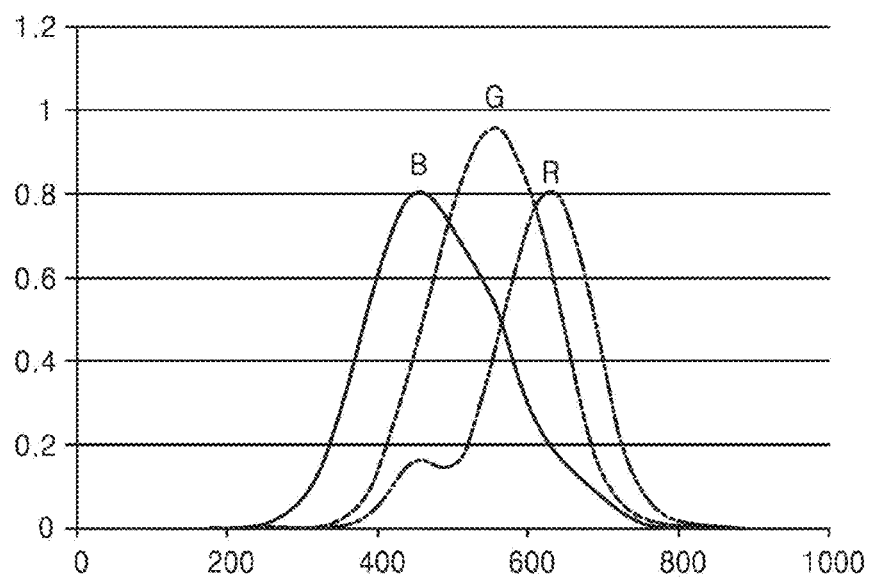
FIG. 14 is a diagram showing spectra of sensitivities of the R, G, and B sensors installed in a CCD.

Referring back to step S110 of FIG. 12, an image is obtained by photographing skin to which the blue light is irradiated. However, as shown in FIG. 13, most (L2) of the blue light irradiated to the skin is reflected from the surface of the skin and the intensity of the reflected light is considerable. Therefore, if the skin is photographed as it is without any treatment, the reflected light L2 exceeds sensitivity of R, G and B sensors of a CCD sensing light to cause a whitening phenomenon. That is, referring to FIG. 14 showing the spectra of sensitivities of the R, G, and B sensors which are installed in the CCD, an element which senses green or red also reacts to light in a blue region. If the reflected light is strong, all the R, G, and B values react to a peak valve to cause the whitening phenomenon. Therefore, in step S110, except for the reflected light region, a skin region to be diagnosed is photographed via a filter through which only light having a longer wavelength band may pass.

Figure 15:
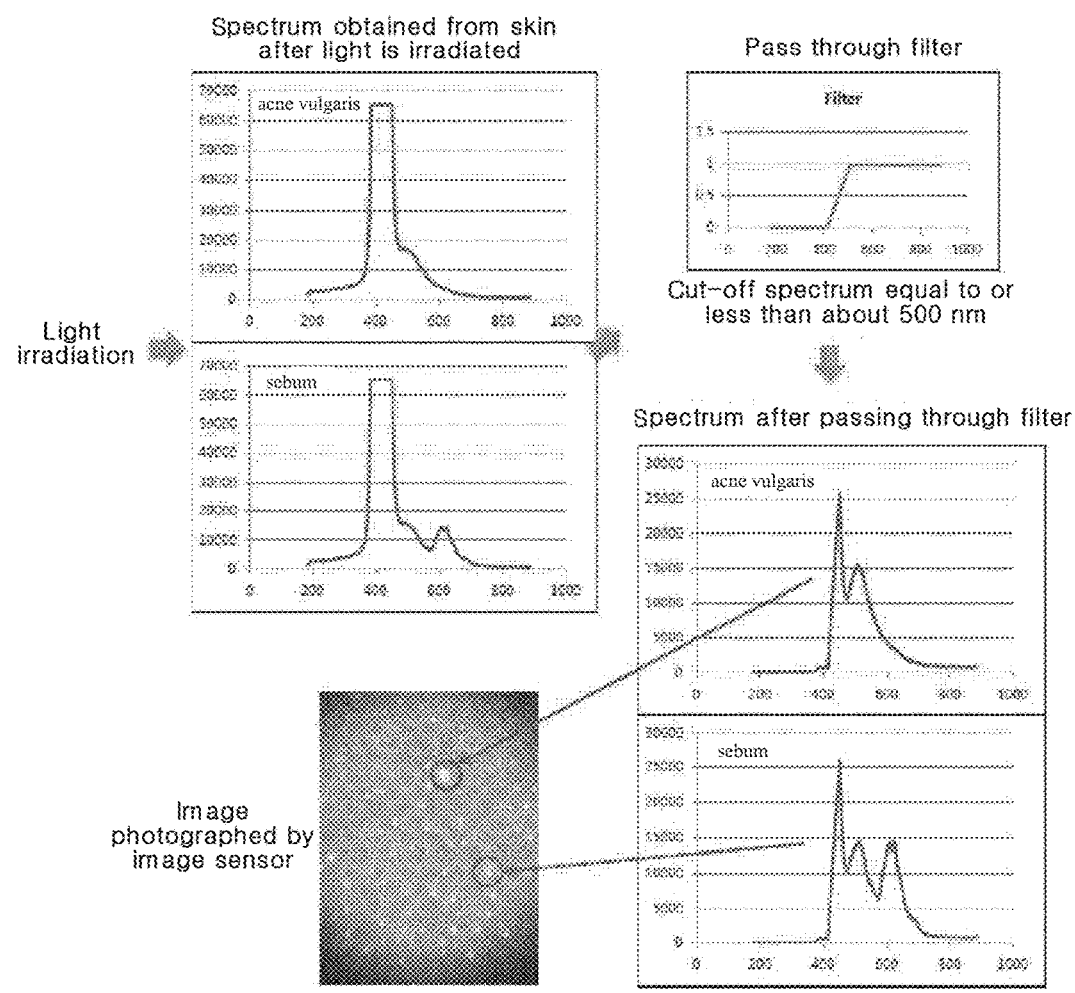
FIG. 15 is a graph showing a spectrum of light emitted from the skin and a spectrum after the spectrum is filtered by a filter.

That is, as shown in FIG. 15, if the intensity of light in the blue light wavelength band is too strong (refer to "spectrum obtained from skin after light is irradiated" of FIG. 15), the R, G, and B sensors may not properly detect light in a spectral domain which has to be properly detected as they detect the intensity of light and react. Therefore, the skin is photographed by a filter installed in an optical path capable of cutting-off the blue light spectral domain without being directly photographed by a sensor such as a CCD, such that the light in the wavelength band which has to be sensed is filtered to be detected (refer to "spectrum after light passes through the filter" of FIG. 15).

Referring back to FIG. 12, RGB values are extracted for each pixel of the photographed image (step S120).

Then, it is confirmed whether the RGB values of the corresponding pixel is in a range in which the inflammatory property caused by the porphyrin generated by the *P. acne* is reflected through the image process, based on the extracted R value, G value, and B value (step S130). For example, the image process may be performed by numerically expressing the RGB values of the corresponding pixel by a predetermined expression f (R, G, B), and confirming whether the thus digitized value exceeds a threshold.

At this time, if the RGB values of the corresponding pixel are in the range in which the inflammatory property due to the *P. acne* which is bacteria inducing acne vulgaris is reflected, the image process is additionally performed to confirm whether the area of the pixel within the range is larger than a reference area (step S140).

If an area of a part where the pixels having the RGB values reflecting characteristics of the *P. acne* contact each other is larger than the reference area, the corresponding area part is recognized as a part where the acne vulgaris occurs or may occur (step S150). If some pixels accidentally have a value exceeding the threshold during the image process due to noise generated from the image sensor at the time of photographing, the process is to exclude the some pixels from the determination of the skin condition. The method for diagnosing acne vulgaris of the present disclosure builds data for the size, the number, the location information or the like of the acne vulgaris while recognizing the acne vulgaris.

After the diagnosis of the acne vulgaris is completed, the photographed image is displayed on a display means, and a circle or an arrow is displayed on a part where acne vulgaris is present to provide convenience for the user to easily confirm the acne vulgaris. For example, as shown in FIG. 16, if the photographed image is displayed as a circle of a dotted line so that the part determined to be acne vulgaris may be easily confirmed, the corresponding location may be easily confirmed.

In the present disclosure, the acne vulgaris is not only displayed, but the size and the number of the acne vulgaris are also recognized to be built as data as described above, and therefore if the number of acnes per unit area exceeds a predetermined number based on the data, an alarm may be provided to users by vibration, sound or the like to inform them that skin cleansing or skin care is needed.

This allows the user to not only visually confirm the location where acne vulgaris will occur with the naked eye by the display, but also obtain information on skin care and prescription of medicines through various messages.

Although the method for diagnosing acne vulgaris of skin described above as the example of the skin diagnosis may perform the skin diagnosis by a fairly simple process. However, to make the skin diagnosis with the simple process, a certain premise is required.

First, when light is irradiated to skin for skin photographing, light other than the light irradiated from the LED that emits the light in the first wavelength band described above, that is, the blue light of about 407 nm, is not irradiated to the skin. If the above-described photographing is performed in a space in which natural light is brightly irradiated, since the light irradiated to the skin already has a wide spectrum, it is difficult to properly detect the autofluorescence phenomenon only by the simple process as described above, which leads to a misdiagnosis.

Second, in order to properly grasp the number of acne vulgaris per unit area which occurs or will occur in skin, it is preferable that all the scales of the image for the skin photographed by the CCD are the same. Of course, the image may be adjusted to the desired scale by using a variety of other indexes, but for the image processing, a new processes need to be added. Also, the image processing may not always be performed accurately, which may be a cause of misdiagnosis.

Third, the spectra of the sensitivities of R, G, and B sensors of the CCD should be grasped. The method for diagnosing acne vulgaris described above diagnoses acne vulgaris based on the RGB values of each pixel. Even if the same skin is photographed, if the characteristics of the CCD are different, there is a difference in the RGB values obtained by the photographing, which may be a cause of misdiagnosis.

In the meantime, the present disclosure does not consider a diagnostic device provided in a dermatological hospital in which the diagnosis should be performed professionally, but rather considers a device that enables a general person to perform a diagnosis himself/herself at home, and therefore there is a problem that hardware costs are high and the economical burden of the system becomes large accordingly. In particular, if a user has to get different devices each time he/she wants to diagnose different skin diseases, the economic burden may increase. Accordingly, the present disclosure provides a device for diagnosing skin which can be used by simply replacing only the camera module according to the kind of skin diseases to be diagnosed without economical burden, by implementing a central processing unit, a memory, an image sensor, and the like, which need not be replaced, as portable terminals such as a smart phone and a tablet already carried by most users while minimizing components which need to be replaced according to the skin diseases.

Figure 17:
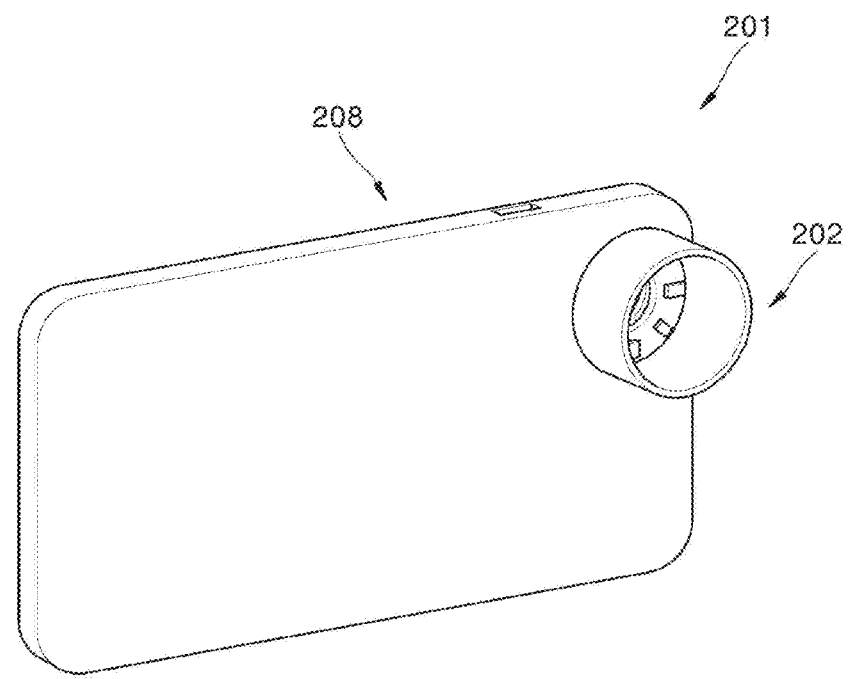
FIG. 17 is a perspective view showing an embodiment of a device for diagnosing skin to which the method for diagnosing skin according to the present disclosure is applicable.
Figures 18A, 18B:
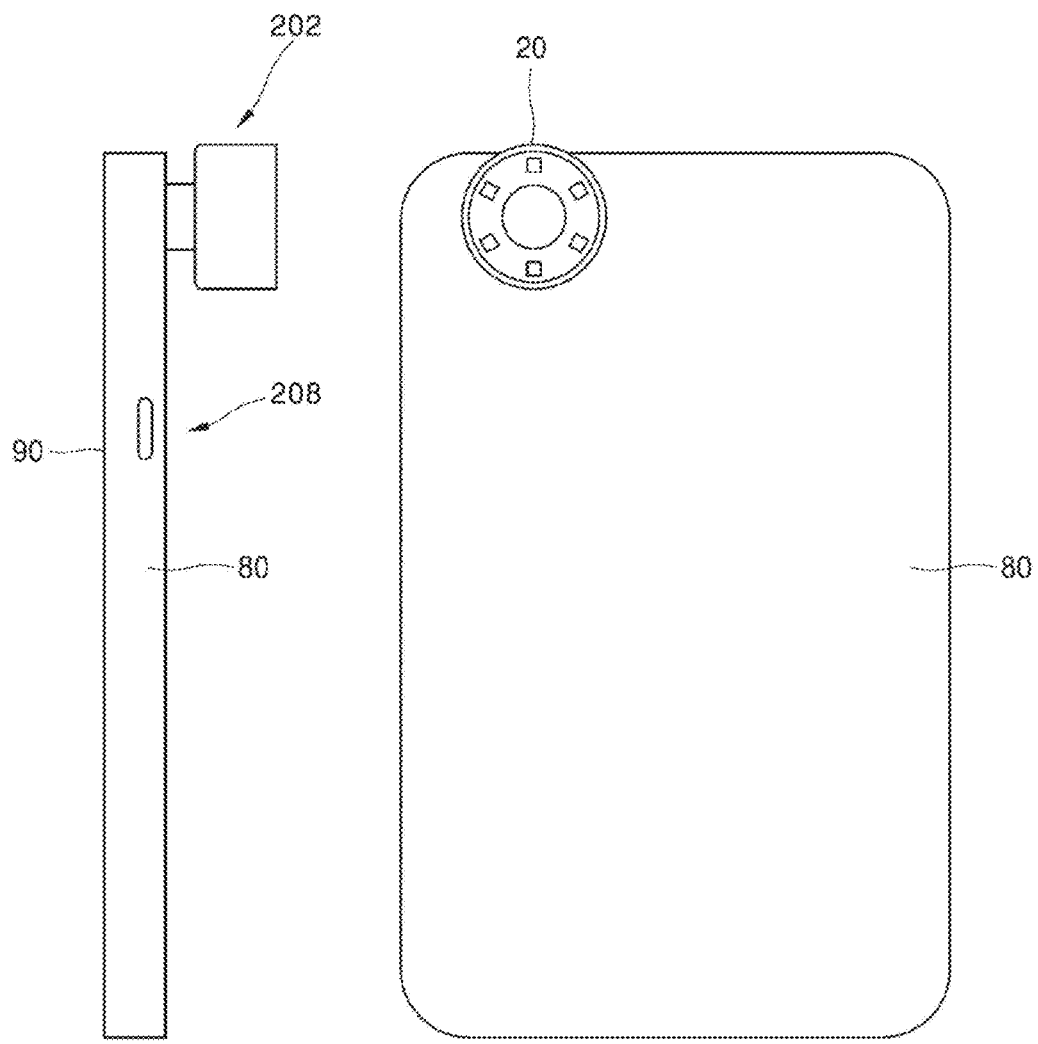
FIGS. 18A and 18B are side view and a front view of the device for diagnosing skin of FIG. 17.
Figure 19:
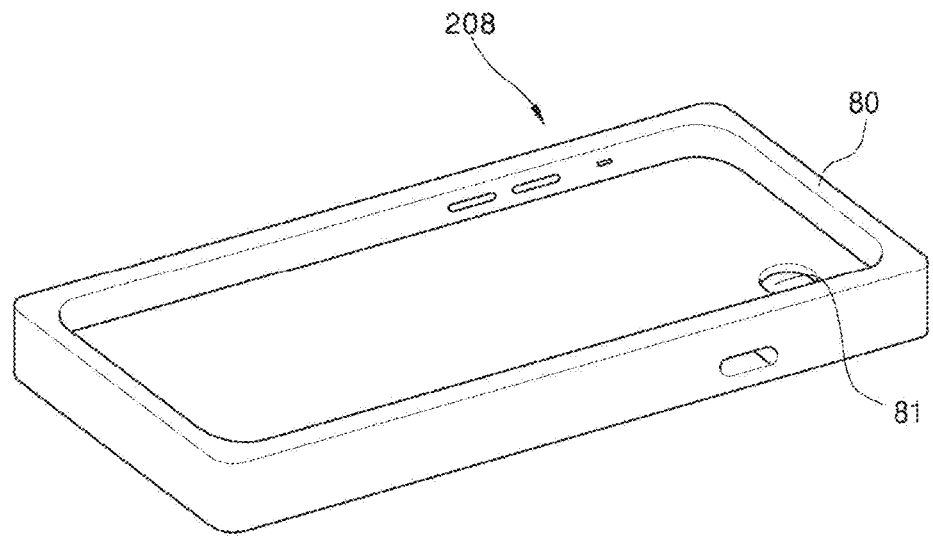
FIG. 19 is a perspective view of a fixing module configuring the device for diagnosing skin of FIG. 17.
Figure 20:
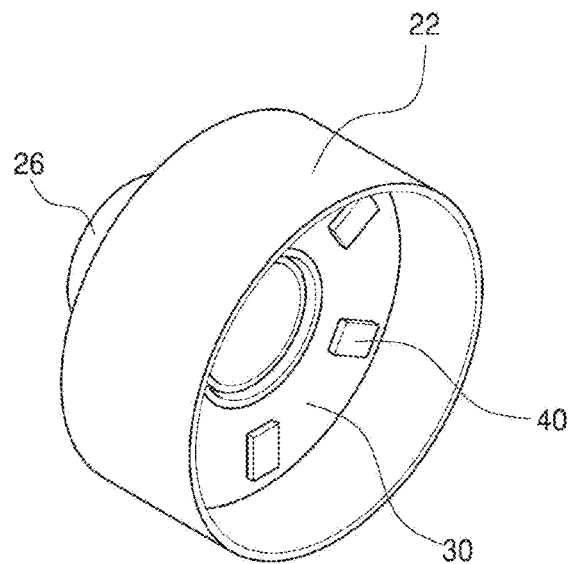
FIG. 20 is a perspective view of a camera module configuring the device for diagnosing skin of FIG. 17.
Figure 21:
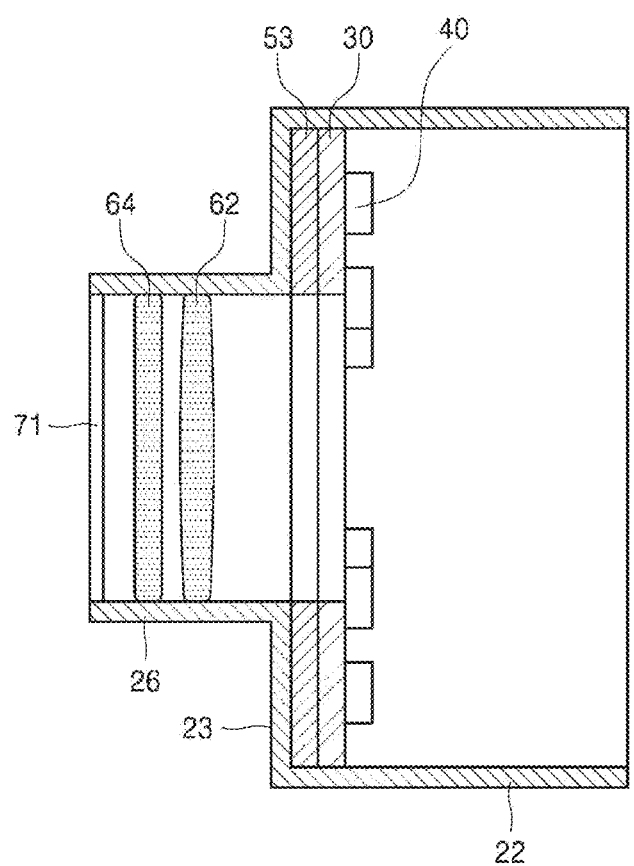
FIG. 21 is a side cross-sectional view of the camera module of FIG. 20.
Figure 25:
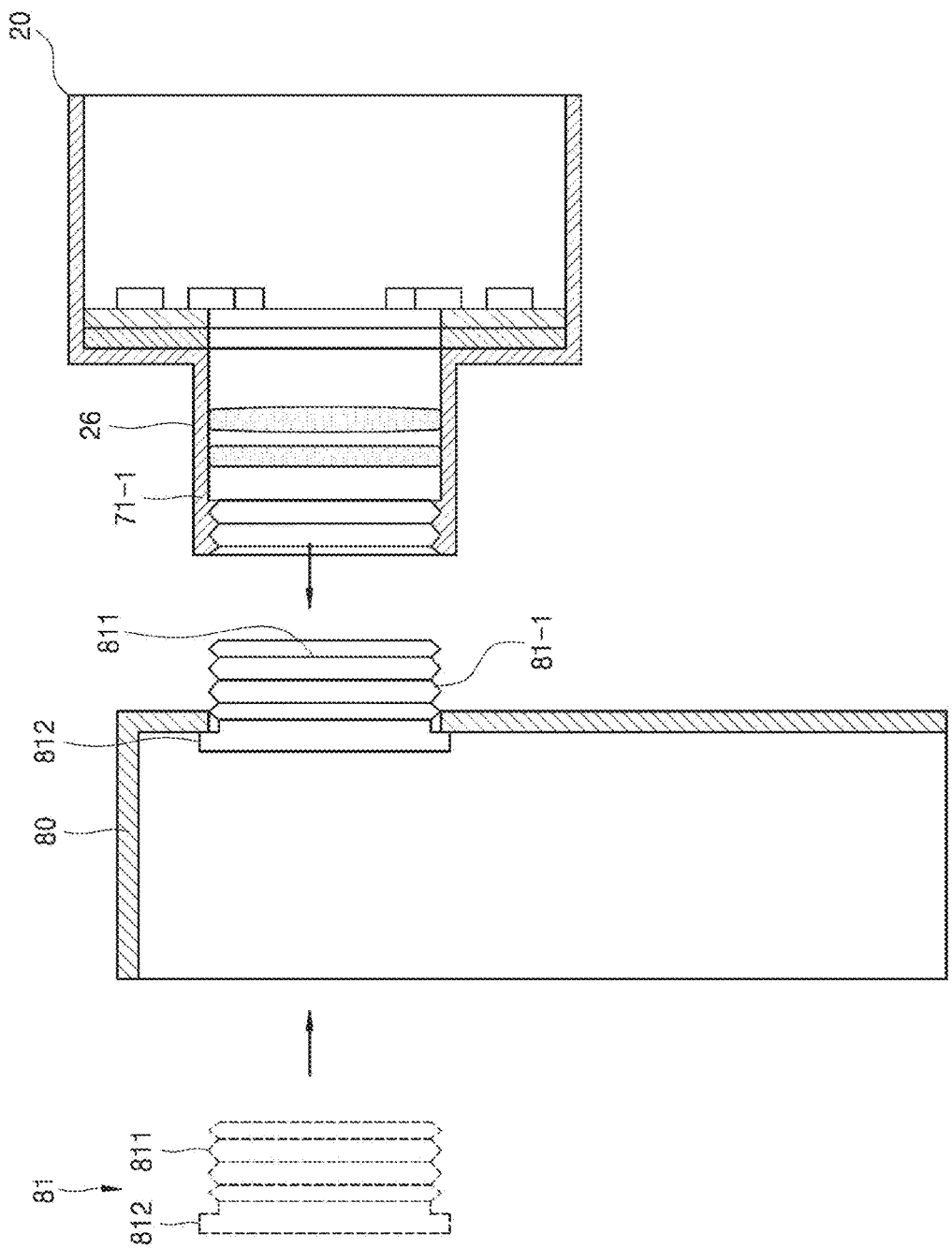
Figure 26:
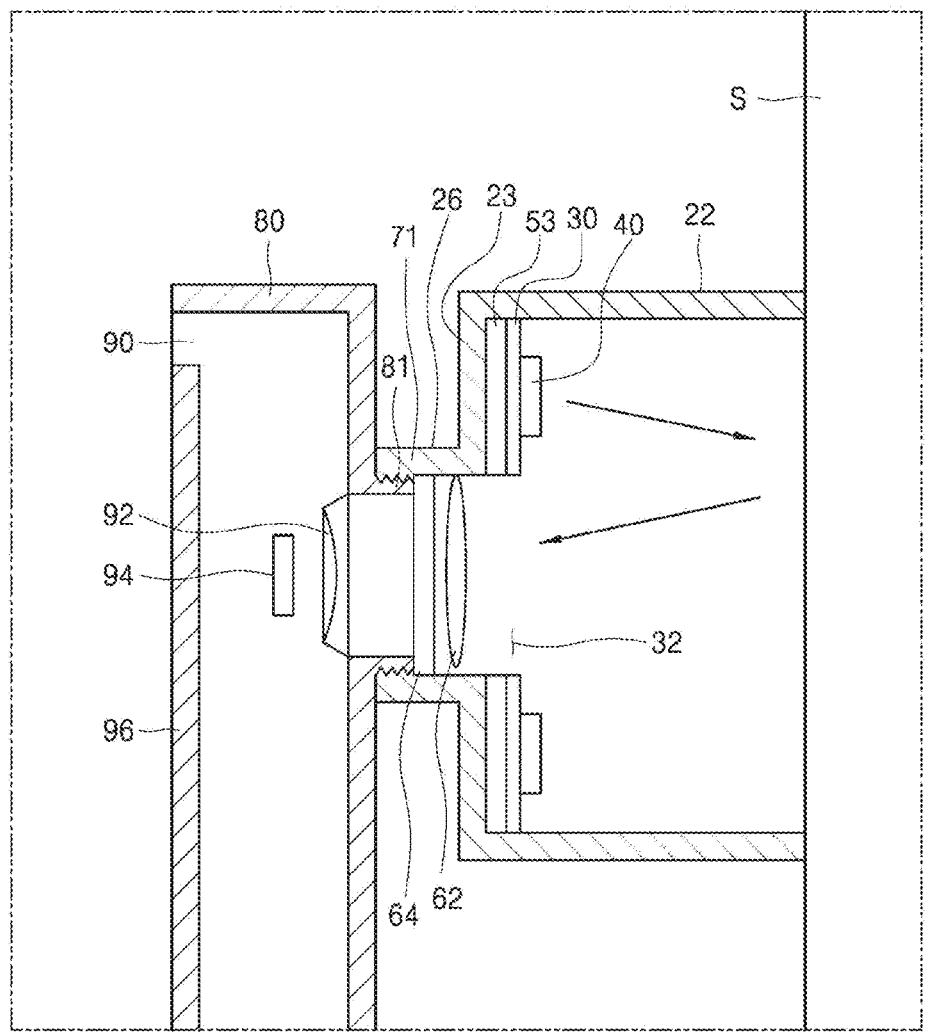
FIG. 26 is a side cross-sectional view of the device for diagnosing skin fastened in the manner shown in FIG. 22.

Hereinafter, an example of the device 201 for diagnosing skin (or skin photographing and image processing device) will be described. FIG. 17 is a perspective view showing an embodiment of a device 201 for diagnosing skin to which the method for diagnosing skin according to the present disclosure is applicable, FIGS. 18A and 18B are a side view and a front view of the device 201 for diagnosing skin of FIG. 17, FIG. 19 is a perspective view of a fixing module configuring the device 201 for diagnosing skin of FIG. 17, FIG. 20 is a perspective view of a camera module 202 configuring the device 201 for diagnosing skin of FIG. 17, FIG. 21 is a side cross-sectional view of the camera module 202 of FIG. 20, FIGS. 22 to 25 are diagrams showing an embodiment of detachment methods of the fixing module 208 of FIG. 19 and the camera module 202 of FIG. 20, and FIG. 26 is a side cross-sectional view of the device 201 for diagnosing skin fastened in the manner shown in FIG. 22.

The device 201 for diagnosing skin (or skin photographing and image processing device 201) of the present disclosure may be implemented by the least components using an image sensor 94 of a portable terminal 90 such as a smart phone or a tablet carried by each person, a central processing unit (CPU), a memory, or the like. As an example of the image sensor 94, the CCD is exemplified in the present disclosure. The image sensor 94 installed in the portable terminal may be configured as an array of a B sensor for detecting blue light, a G sensor for detecting green light, and an R sensor for detecting red light.

The device 201 for diagnosing acne vulgaris according to the embodiment of the present disclosure includes the portable terminal 90, the camera module 202 and the fixing module 208 for fixing the camera module 202 to the portable terminal 90.

The fixing module 208 serves to fix the portable terminal 90 and the camera module 202 to each other. The fixing module 208 includes a base 80 fixed to the portable terminal 90 and a first detachable opening 81 for fixing the camera module 202. For example, the base 80 may be a case for covering the portable terminal to protect the portable terminal from an impact or the like. In the case, a location corresponding to a part where the camera portion of the portable terminal is located is provided with a through hole. The first detachable opening 81 fastened with or separated from the camera module 202 to be described later is formed around the through hole. The first detachable opening 81 may be integrally formed with the base 80 (see FIGS. 22 to 24). Since the first detachable opening 81 is formed in a separated type, when the camera module 202 to be described later is to be fastened to the base 80, the first detachable opening 81 may be fitted into the base 80 (see FIG. 25).

An inside of the camera module 202 is provided with, as its casing, a housing (barrel 20) for housing various components. The housing 20 includes a hollow cylindrical large barrel portion 22 that has a tip part contacting a periphery of the skin to be photographed to prevent light other than the light irradiated from the LED 40 from being irradiated to skin to be photographed and has a relatively larger diameter, a hollow cylindrical small barrel portion 26 that has a base end part fastened with the first detachable opening 81 and fixed and is provided with optical components performing an optical operation on light on an optical path through which the light emitted from skin is incident on the image sensor 94 of the portable terminal 90, and an annular plate-shaped stepped portion 23 that connects between end parts at which the large barrel portion and the small barrel portion face each other.

The housing (barrel) 20 may be integrally made of synthetic resin. The large barrel portion 22 of the housing may have approximately 30 mm in diameter and 14 mm in height, and the diameter and height of the small barrel portion 26 may be determined corresponding to the optical lens 92 and the image sensor 94 of the portable terminal used together.

The inside of the housing (barrel 20) is provided with a substrate 30 that is provided with a control circuit for controlling an operation of various components besides the LED. The substrate used in the present disclosure is provided on an inner surface of the above-described stepped portion 23 and has an annular plate shape like the stepped portion 23. A center of the substrate 30 is provided with a circular hole 32, and a diameter of the hole has a dimension corresponding to an inner diameter of the small barrel portion 26. A front face of the annular substrate 30 is provided with an LED 40 that irradiates the light in the first wavelength band toward a tip part of the opened large barrel portion 22. The LEDs 40 are mounted around the annular substrate portion at regular intervals, so the directivity need not be considered when the camera module 202 is fixed to the portable terminal 90.

The light in the first wavelength band irradiated from the LED 40 installed in the camera module 202 used for diagnosing acne vulgaris is blue light having a peak wavelength of 407 nm. However, the peak wavelength of the light in the first wavelength band necessary for acne vulgaris diagnosis is not necessarily limited to 407 nm, and the light may be blue light or near-ultraviolet light having a peak wavelength ranging from 380 nm to 420 nm. This corresponds to the width of the spectrum corresponding to half of the maximum absorption rate in the absorption spectrum of the coproporphyrin 3 shown in FIG. 11. Therefore, if the peak wavelength of the light irradiated from at least the LED is within the range of 380 nm to 420 nm, the light energy absorption efficiency of the porphyrin existing in the skin can be secured to a considerable level.

The substrate 30 is provided with the control circuit for controlling the operation of the LED and a switch for turning on and off the camera module 202. In addition, the substrate 30 is electrically connected to a battery 53 which is housed in the housing 20 together. The battery 53 has an annular shape as shown and may be connected to the substrate 30 so as to be disposed between the stepped portion 23 and the substrate 30. The substrate 30 is also provided with a power supply controller for controlling charging or discharging of the battery. The battery 53 is a secondary battery such as a lithium polymer battery, and may perform charging and discharging reversibly therein. The substrate 30 is provided with a charging terminal for connecting an external power supply for charging the battery.

In addition, the substrate is provided with a Bluetooth chipset that transmits/receives a control signal to/from a main body of the portable terminal. A program for using the portable terminal as the device for diagnosing skin may be installed in a portable terminal in the form of an application. For example, if a user presses a photographing button after driving the program, a control signal for the LED 40 which is generated from the portable terminal is transmitted to the control circuit of the substrate 30 through a Bluetooth protocol, so the LED 40 may be turned on. Then, the program may cause the image sensor 94 of the portable terminal 90 to photograph an image within a time period during which the LED 40 is turned on.

The control signal does not necessarily have to be transmitted in the Bluetooth manner. For example, a USB terminal on the portable terminal is connected to the charging terminal on the substrate 30, and the charging terminal is supplied with power from the USB terminal to be used for operating the LED or to charge the battery, and may be configured to be supplied with an LED control signal from the USB type terminal and transmit the LED control signal to the LED control circuit. In addition, it is possible to receive a control signal through an earphone or headphone connection terminal of the portable terminal. As described above, according to the present disclosure, the control signal may be transmitted/received between the portable terminal 90 and the camera module 202 by applying various near field communication protocols such as wired or wireless (WiFi, NFC, etc.) near field communication protocols.

Alternatively, the LED 40 may be driven by being simply turned on and off only by a switch. In other words, the user may control the LED by turning on the switch when he/she wants to diagnose the skin and turning off the switch after the photographing ends.

Further, the camera module 202 has a structure in which the battery 53 is omitted, and the charging terminal may be used as a power supply terminal. For example, the USB terminal of the portable terminal 90 and the power supply terminal of the camera module 202 which are described above may be connected in the wired manner to perform a supply of power in such a manner that the portable terminal 90 is supplied with power. Of course, as described above, it is possible to receive the LED control signal from the USB terminal and transmit the received LED control signal to the LED control circuit.

A wide-angle lens 62 and a long pass filter 64 are each fitted in the small barrel part 26 in order to be fixed. The embodiment exemplifies that the wide-angle lens 62 and the long pass filter 64 are fixed to the inner surface of the small barrel part by an interference fit. However, it is needless to say that other conventional fixing methods are also applicable.

The wide-angle lens 62 is to adjust a focal distance to the image sensor 94 of the portable terminal 90 even at the low height of the housing. Therefore, the image of the skin may be focused on the image sensor 94 by the wide-angle lens 62 and the optical lens 92 of the portable terminal 90.

In addition, in order to diagnose acne vulgaris according to, for example, the diagnosis method, the long pass filter 64 may be configured to pass only light having a wavelength of more than 500 nm so that the light in the second wavelength band is included. That is, the long pass filter 64 serves to exclude the blue light which is the light in the first wavelength band irradiated to the skin, and to pass not only the green light but also light having a longer wavelength than that of the green light so that the light in the second wavelength range is included. Therefore, each of the RGB sensors of the image sensor 94 may react to strong reflected light in the vicinity of 407 nm which is directly reflected from the surface of the skin and is the light in the first wavelength band to prevent the corresponding pixels from becoming white.

The present disclosure exemplifies that the wide-angle lens 62 and the long pass filter 64 are provided separately. However, in the actual manufacturing, the wide-angle lens 62 and the long pass filter 64 may be integrally manufactured. For example, the wide-angle lens 62 is designed to be made of a PMMA resin having excellent light transmittance and is manufactured by injection molding, and may also perform the function of the long pass filter by mixing a yellow-based pigment, which absorbs the wavelength of the first wavelength band, with a resin before the injection molding. According to the method, the number of assembled parts is reduced. Since the number of parts is reduced, it is possible to reduce the volume of the product and lower the manufacturing costs. That is, the lens has the shape of the wide-angle lens 62, and may also perform the function of the long pass filter 64 by allowing a medium of the lens to absorb the light in the first wavelength band.

The housing 20 having the above-described various components may be fixed to the portable terminal 90 by being fixed to the base 80, which is the case of the portable terminal, as described above.

Figure 22:
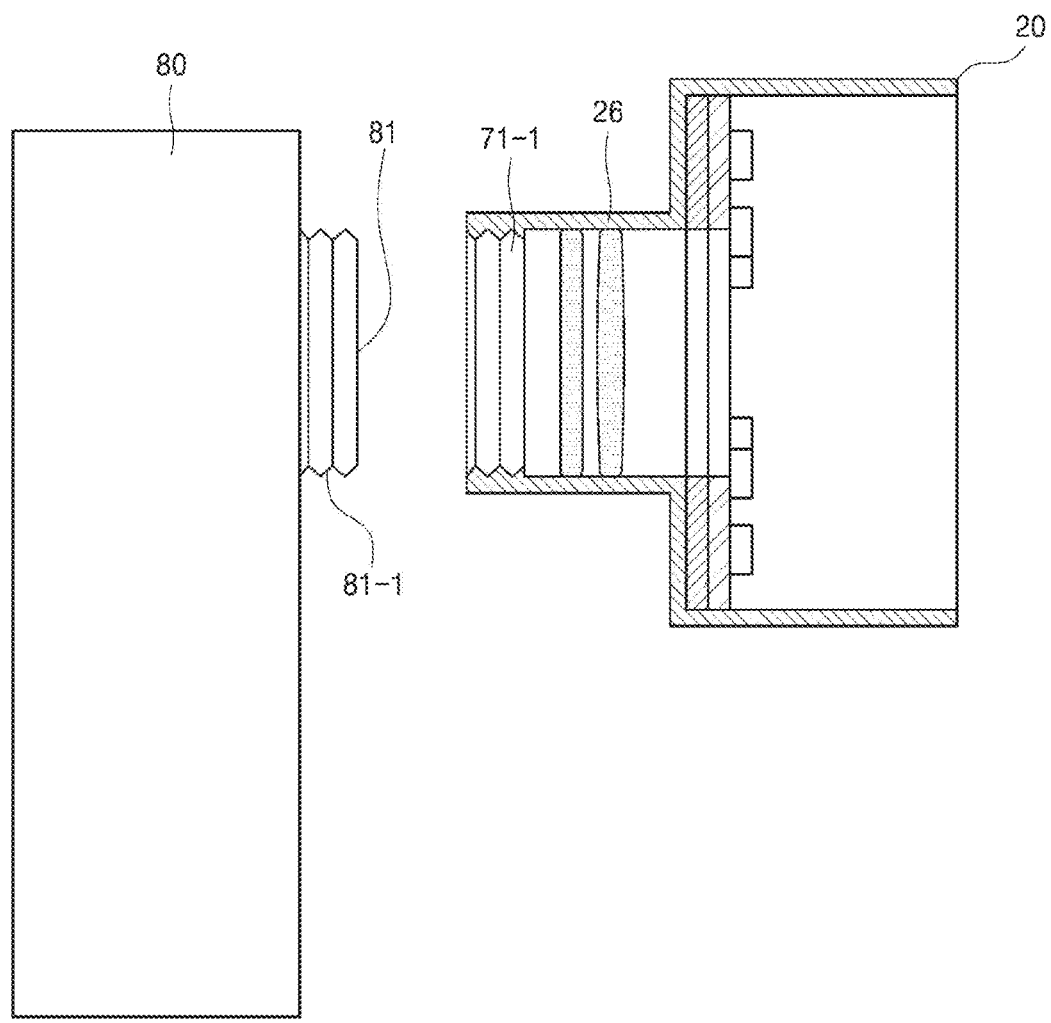
FIGS. 22 to 25 are diagrams showing an embodiment of detachment methods of the fixing module of FIG. 19 and the camera module of FIG. 20.

Referring to FIG. 22, a second detachable opening 71 located at the base end part of the small barrel portion 26 is provided with a female screw 71-1, and the first detachable opening 81 of the base 80 is provided with a male screw 81-1 that is fitted in the female screw 71-1, so the camera module 202 may be fixed to the portable terminal 90 by being fixed to the base 80 in a screwed manner. According to such a fastening and separating method, the camera module 202 may be simply fastened with the base 80 only for the skin diagnosis. When a plurality of different camera modules are provided according to the purpose of diagnosis, the camera module corresponding to the skin disease to be diagnosed may be selectively fastened with the base 80 to perform the skin photographing. Then, the user may select and execute a program that allows the portable terminal to perform photographing and diagnosis for the skin disease to be currently diagnosed or may select the skin disease to be diagnosed within the program after the program is executed.

Figure 23:
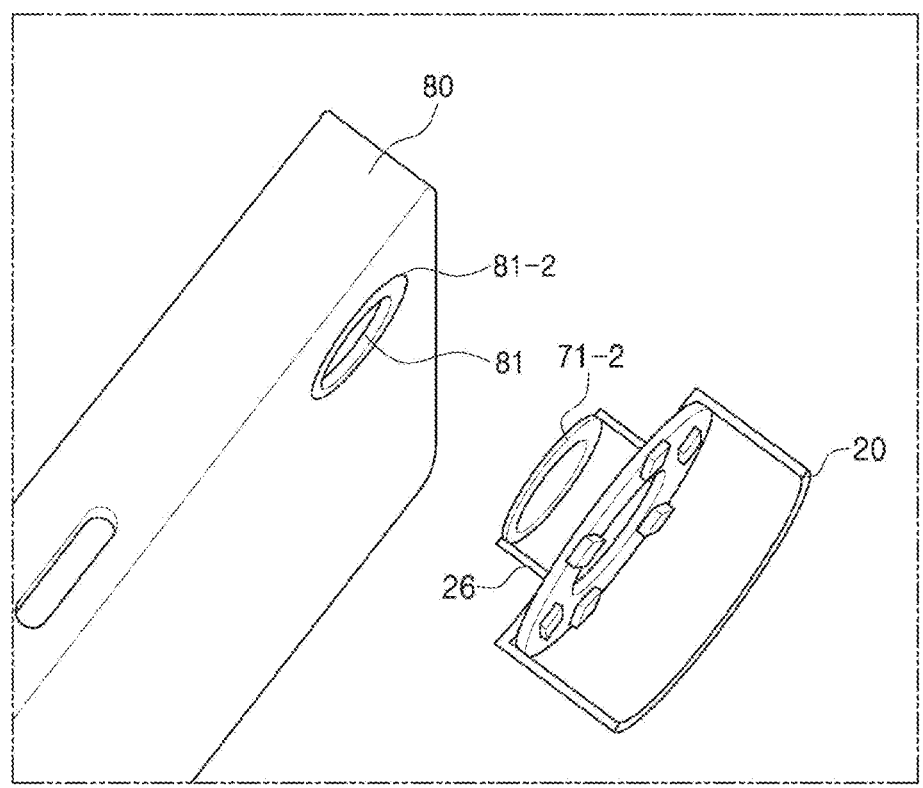

Next, referring to FIG. 23, the second detachable opening 71 located at the base end part of the small barrel portion 26 is provided with a magnet 71-2, and the first detachable opening 81 of the base 80 is provided with a magnet 81-2 that has attraction to the magnet 71-2, so the camera module 202 can be fixed to the portable terminal 90 by being fixed to the base 80 in the magnet fixing manner. Of course, protrusions, grooves and the like having a shape corresponding to each other are each formed on the surfaces where the base 80 and the small barrel part 26 face each other, so the protrusions are fitted in the grooves, thereby more strengthening the fastening force of the above two components.

Figure 24:
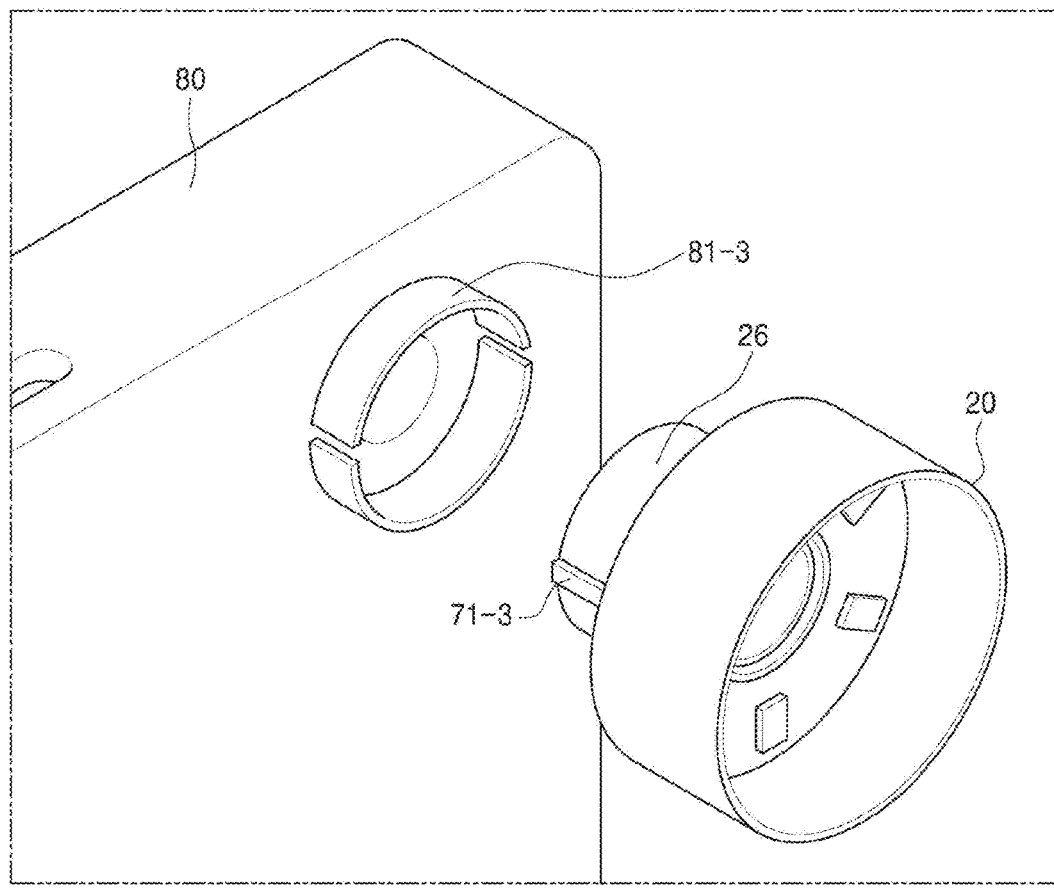

Next, referring to FIG. 24, the second detachable opening 71 located at the base end part of the small barrel portion 26 is provided with a fitting portion 71-3, and the first detachable opening 81 of the base 80 is provided with a fitting portion 81-3 so that the fitting portion 71-3 is fitted therein, so the camera module 202 can be fixed to the portable terminal 90 by being fixed to the first detachable opening 81 of the base 80 in the interference fit manner. As shown, the fitting portion 71-3 is provided with a protrusion and the fitting portion 81-3 is provided with a groove in which the protrusion is tightly fitted, so the protrusion is fitted in the groove, thereby more strengthening the fastening force of the above two components.

FIGS. 22 to 24 show the example in which the base 80 and the first detachable opening 81 are integrally formed. However, the first detachable opening 81 can be separated from the base 80, so the first detachable opening 81 can be used while being fitted in the base only when the camera module 202 is fixed to the base. For example, as shown in FIG. 25, the first detachable opening 81 is fitted in the through hole of the base 80 on the back face of the case, and the camera module 202 can be fitted in the first detachable opening 81 on the surface of the case to be fixed. At this time, the first detachable opening 81 includes a detachable portion 811 which is a portion fastened with the second detachable opening 71 of the camera module 202 and a base fixing portion 812 which is a portion fixed to the base 80. A diameter of the base fixing portion 812 is larger than that of the through hole of the case, so the base fixing portion 812 can not pass through the through hole. FIG. 25 shows that the first detachable opening is separated from the base in the case of the screwed manner. However, it is needless to say that the separated structure can be applied even to the other methods described above.

If the housing 20 is fixed to the portable terminal 90, as shown in FIG. 26, the housing 20, that is, the long pass filter 64, the wide-angle lens 62, and the circular hole 32 of the substrate are axis-aligned together with the image sensor 94 and the optical lens 92 of the portable terminal 90. As shown in FIG. 26, the tip part of the large barrel portion 22 may photograph the skin while being in close contact with the skin S. That is, the large barrel portion 22 contacts the skin, and thus the focal distance to the image sensor 94 is fixed to the distance between the image sensor 94 and the tip part of the large barrel portion 22. In addition, the large barrel portion 22 is made of an opaque substance, so that it is possible to prevent light from being irradiated to a space in the barrel from other light sources other than the LED 40. That is, the inside of the barrel satisfies a dark room condition in which there is no light source other than the LED 40.

Therefore, a skin contact type large barrel portion 22 of the device for diagnosing skin of the present disclosure may make the scales of the images of the skin photographed by the image sensor 94 the same while satisfying the condition that lights other than the light irradiated from the LED emitting the light in the first wavelength range, for example, the blue light in the vicinity of 407 nm are not irradiated together.

Therefore, if the photographed enlarged images are composed, it is possible to prevent errors and distortions that may occur during the composition process.

The reason why the barrel portion is meaningful in the present disclosure is that the photographing assumed in the present disclosure is taken in consideration of close-up.

Techniques for photographing landscapes at different angles and composing the photographed landscapes into panoramic images have been already widely used. The principle of the composition is that a pattern in which two images overlap each other is searched and two images are attached together based on the searched pattern to be one image. However, since the landscape image is photographed at a long distance and therefore a distance between the camera for photographing and a subject is considerable or very long, making the camera to be slightly closer or farther away from the subject does not affect the scale. However, when the photographing is performed at a distance of only about 1 to 3 cm like the skin of the present disclosure, even a distance error of only 1 mm considerably affects the scale.

Therefore, according to the embodiments of the present disclosure, the photographing is performed by bring the tip part of the barrel into contact with the skin to be photographed by using the barrel of the camera module 2, so all the scales between the photographed image and the skin may be the same.

In addition, unlike the landscape image, since the close-up photographing performed in the present disclosure largely changes an illuminance or hue of the irradiated light depending on the location and direction of the subject or the camera, in order to match the illuminance, hues, or the like of the respective photographed images each other, all the locations or directions of the subject or the camera need to be under the same environment. Here, the above-described barrel irradiates the same light at the same location of the LEDs 40, prevents light sources other than the LED from being irradiated to the skin, and continuously maintains the same photographing distance, so the illuminance and hues of all the photographed images become uniform.

Therefore, if the photographing is performed by the camera module 202 of the present disclosure, all of the above-mentioned problems may be solved.

The images photographed by the camera module of the present disclosure can be composed based on the shape and arrangement of wrinkles and pores of the skin. Such an image composition program may be, for example, an application installed in the portable terminal.

Meanwhile, the camera module 202 can be used while being attached to various portable terminals. However, when the camera module 202 is used while being attached to different devices, the spectra of the sensitivities of the R, G, and B sensors of the image sensor installed in the corresponding device need to be grasped. That is, since the sensitivities of the R, G, and B sensors are different for each device, the R, G, and B values processed are different in the photographed images even if the same skin is photographed. Therefore, an expression f (R, G, B) reflecting the sensitivities of the R, G, and B sensors which are different for each device is required. By the way, manufacturers of the camera module 202 may provide the above expression as an application of the portable terminal such a smart phone and a tablet. That is, the applications implementing the image process to which the spectrum information of the sensitivities of the R, G, and B sensors grasped for each device is reflected are uploaded on an app store, and users download the uploaded applications, install the downloaded applications in the portable terminal, and then use the applications. As a result, the users may actively cope with various image sensors having different attributes.

Therefore, users purchase the camera modules 202 each which can diagnose skin diseases that they want to diagnose, install the purchased camera modules in their own smart phones and install applications in their own smart phones, thereby implementing the diagnosis device. In addition, the camera module 202 can be implemented by the least components described above, and therefore the price of the camera module 202 may be lowered. Therefore, this makes it possible for users to use the camera module conveniently at home.

Hereinafter, an example of a method for diagnosing a skin disease, for example, acne vulgaris, using such a device will be described.

The user installs a program executing diagnosis of acne vulgaris in his/her own portable terminal 90. The camera module 202 is installed on the base 80 of the portable terminal 90 so that the camera module 202 and the optical lens 92 of the portable terminal 90 are aligned and fixed.

The user turns on the switch of the camera module 202 and drives the program of the portable terminal 90 and connects the camera module 202 and the portable terminal 90 via Bluetooth. Then, the program loads the characteristics of the image sensor 94 used for the corresponding model and the threshold for determination on whether the acne vulgaris occurs into the memory, according to the model of the corresponding portable terminal 90.

The user contacts the tip part of the large barrel part 22 to the skin at which acne vulgaris is to be diagnosed acne and presses the photographing button on the portable terminal 90. Then, the control signal is transmitted from the portable terminal 90 to the camera module 202 via the Bluetooth protocol, and the LED control circuit and the power supply controller provided on the substrate 30 are operated to turn on the LED. The portable terminal 90 photographs the skin using the image sensor 94 while the LED is turned on. Then, the image photographed by the image sensor 94 detects light having a wavelength of 500 nm or more, and generates RGB values for each pixel.

The RGB values generated for each pixel are stored in the memory of the portable terminal. The central processing unit of the portable terminal performs the image process on the photographed RGB values and compares values calculated by the RGB values of each pixel with the reference value to determine whether the corresponding pixel part is a part having a relation with acne vulgaris. Then, it is determined whether the area exceeds a predetermined reference.

The program of the portable terminal provides a mark informing a location where acne vulgaris has occurred or is highly likely to occur on the image photographed by the image sensor 94 and displays the mark on the display 96 of the portable terminal 90.

Then, the user may watch the display of the portable terminal, and determine that the area indicated by the light in the vicinity of 520 nm is a part where the inflammation will occur or the acne vulgaris has occurred. For reference, even the sebum in the pores is expressed by yellow or red, which is also noticeable.

In addition, if the number of outbreak (possible) points of acne vulgaris per unit area which becomes a reference is equal to or higher than a predetermined level, a method for informing a user of it in a manner such as sound or vibration or a visual manner through a display and prescribing or managing skin depending on a current skin condition may be proposed.

Meanwhile, the present disclosure may satisfy the photographing conditions and further display or attach markers of a certain shape to the skin, and compare the locations of the markers displayed on the composed image with the markers displayed on the actual skin, thereby very conveniently matching the composed image with the actually photographed skin.

Figure 27:
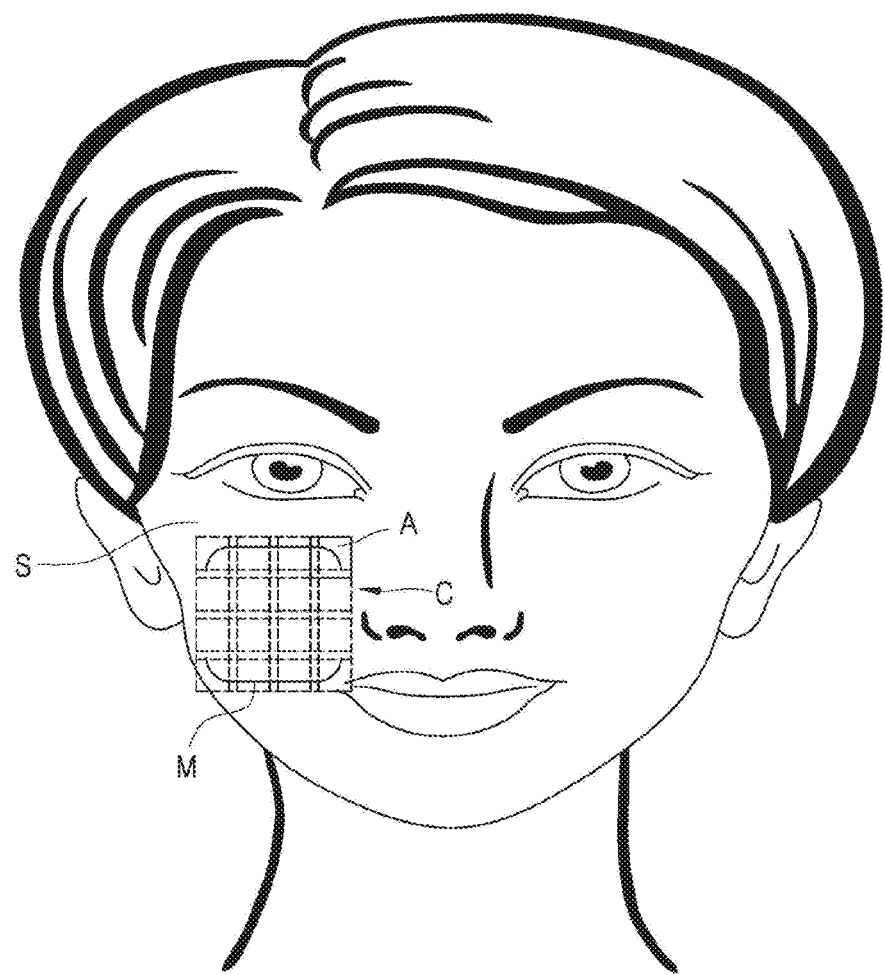
FIG. 27 is a diagram showing a region where a marker is displayed on the skin and the circumference of the marker is enlarged and photographed and a region which the composition is made to be displayed as one.
Figure 28:
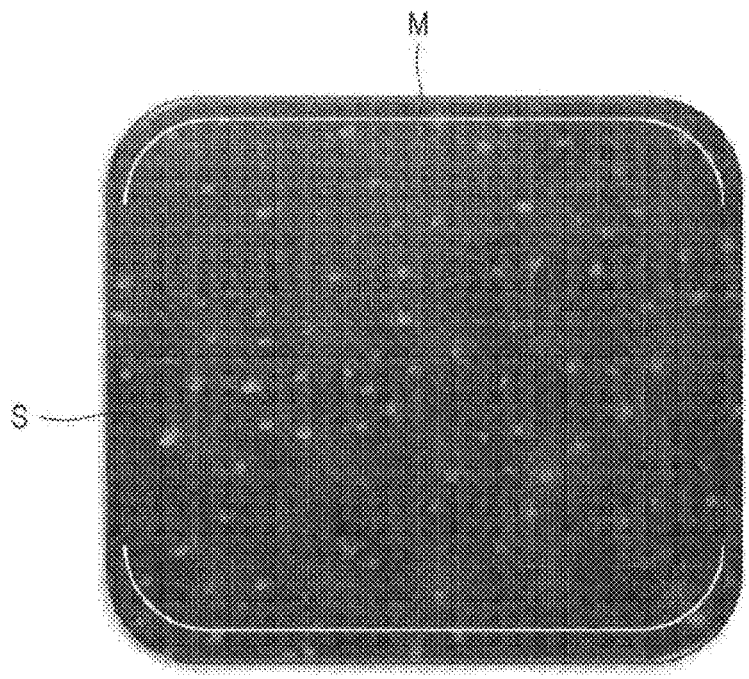
FIG. 28 is a photograph showing a composed image, including a marker.

FIG. 27 is a diagram showing a region where a marker is formed on the skin and the circumference of the marker is enlarged and photographed and a region which is composed and displayed as one and FIG. 28 is a photograph showing a composed image, including a marker.

Referring to FIG. 27, if the skin is photographed using the above-described device 1, a marker M is displayed on the skin S to be photographed, and then a photographing region C to be composed, including the marker, is divided into several regions A, so images are superimposed little by little and photographed. The embodiment of the present disclosure exemplifies that photographing is performed 16 times in four rows×four columns in length and breadth. The marker M is displayed on skin by various methods, such as a method of directly drawing the marker M on the skin, a method of stamping the marker M on the skin with a stamp or the like, and a method of temporarily sticking a sticker or the like on the skin.

If the marker is displayed in this way, it is much easier to align the orientations of various images from the markers even if the device 201 is photographed while slightly rotating. In addition, the marker is displayed and thus the image composition may be more accurate.

Referring to FIG. 28, the marker is displayed on the composed image as shown. Therefore, even if the composed image is displayed on the display while being greatly enlarged, the user may accurately match the composed image with the photographed skin.

Figure 29:
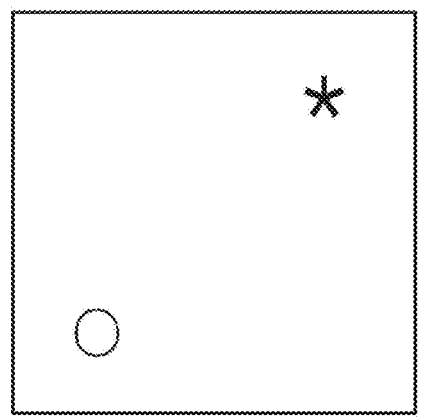
FIGS. 29 and 30 are diagrams showing other embodiments of the marker.

FIG. 29 is another example of the marker. If a first marker and a second marker having two different shapes are placed at two different points, the distance and the direction are all matched. In addition, if the two markers placed at two different points have a difference enough to be distinguished from each other, the two markers do not necessarily have to be the same shape. For example, if the two markers have different sizes, the colors of the two markers may be different.

Figure 30:
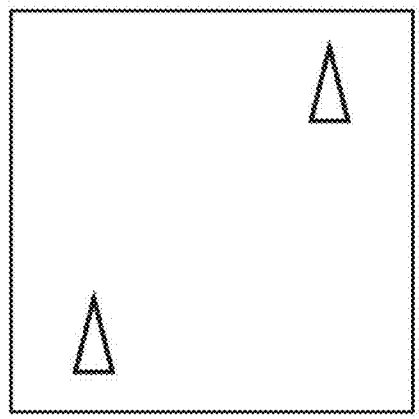

FIG. 30 is another example of the marker. Even if the markers have the same shape, if the shape has directivity and is placed at two different points, the distance and the direction are all matched.

More preferably, the markers may be displayed at edges of the area so that the entire area of the skin to be photographed may be confirmed.

Hereinafter, the device for photographing skin and the image processing method as described above and a process of photographing skin by the implemented device and matching the photographed skin with actual skin and confirming whether the matching is made will be described.

The user installs a program, which can control photographing of skin and compose the photographed images, in his or her own portable terminal 90 The camera module 2 is installed on the base 80 of the portable terminal 90 so that the camera module 2 and the optical lens 92 of the portable terminal 90 are aligned and fixed.

The user turns on the switch of the camera module 202 and drives the program of the portable terminal 90 and connects the camera module 202 and the portable terminal 90 via Bluetooth. Then, the user displays the marker M on the skin to be diagnosed.

Next, the diagnosis area C of the skin S including the marker M is divided into a plurality of enlarged photographing areas A and photographed.

If all the photographing has been completed and then the images are instructed to be composed by the program, all the images are composed to be one large image.

Then, the image may be displayed on the display 96 of the portable terminal 90.

Figure 31:
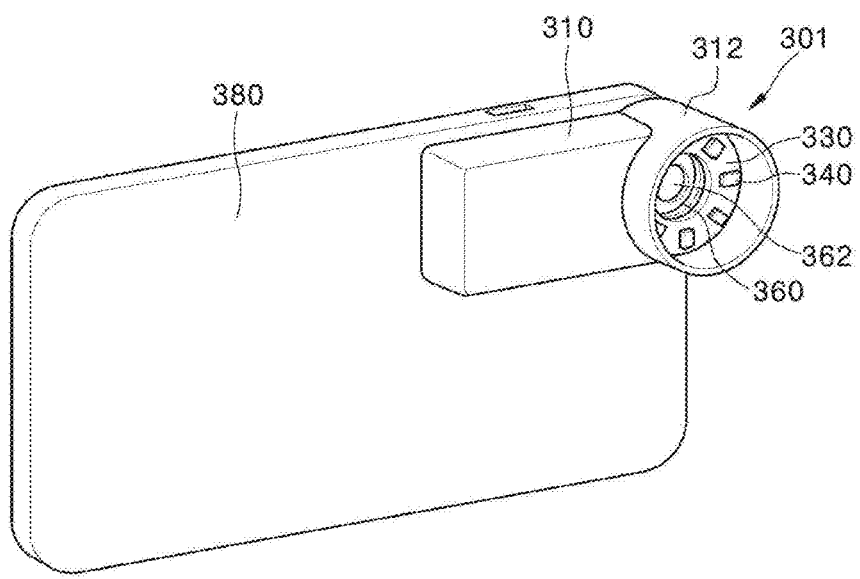
FIG. 31 is a perspective view showing another embodiment of a diagnosis device to which the method for diagnosing acne vulgaris according to the present disclosure is applicable.
Figure 32:
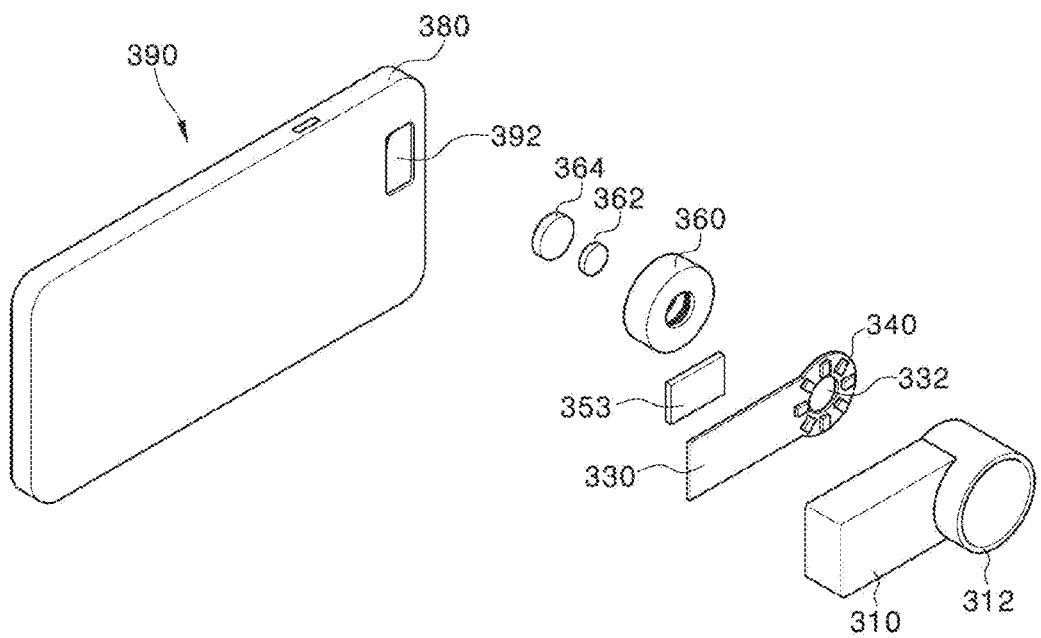
FIGS. 32 and 33 are exploded perspective views of the diagnosis device of FIG. 31 viewed from different directions.
Figure 33:
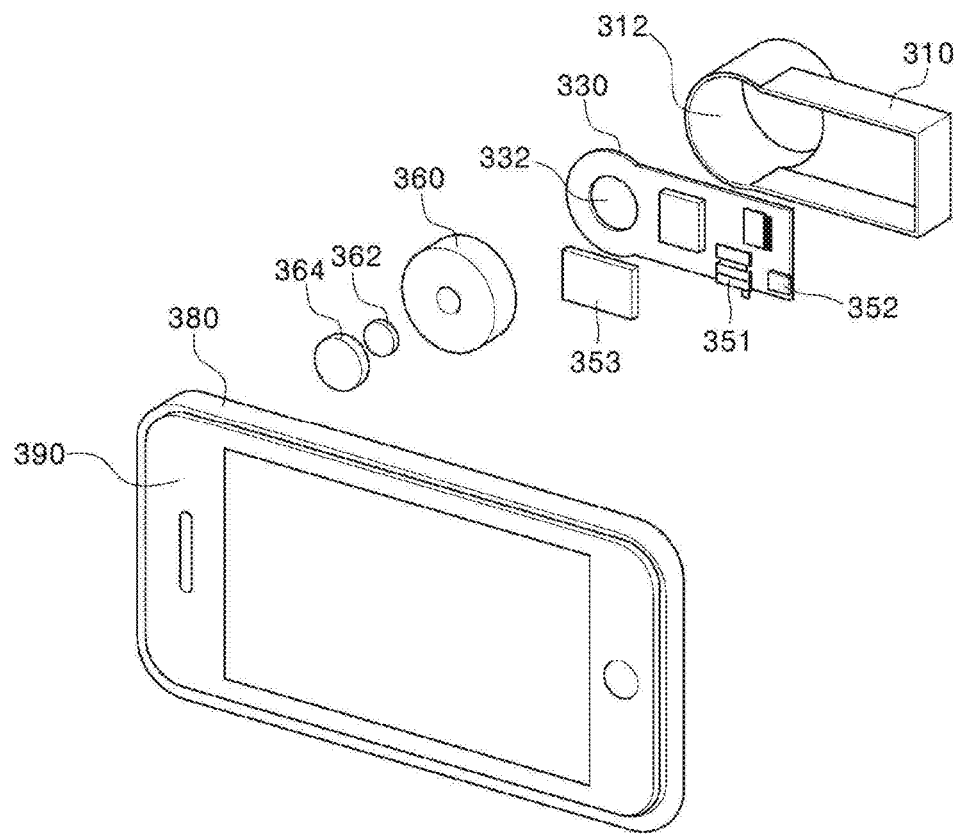
Figure 34:
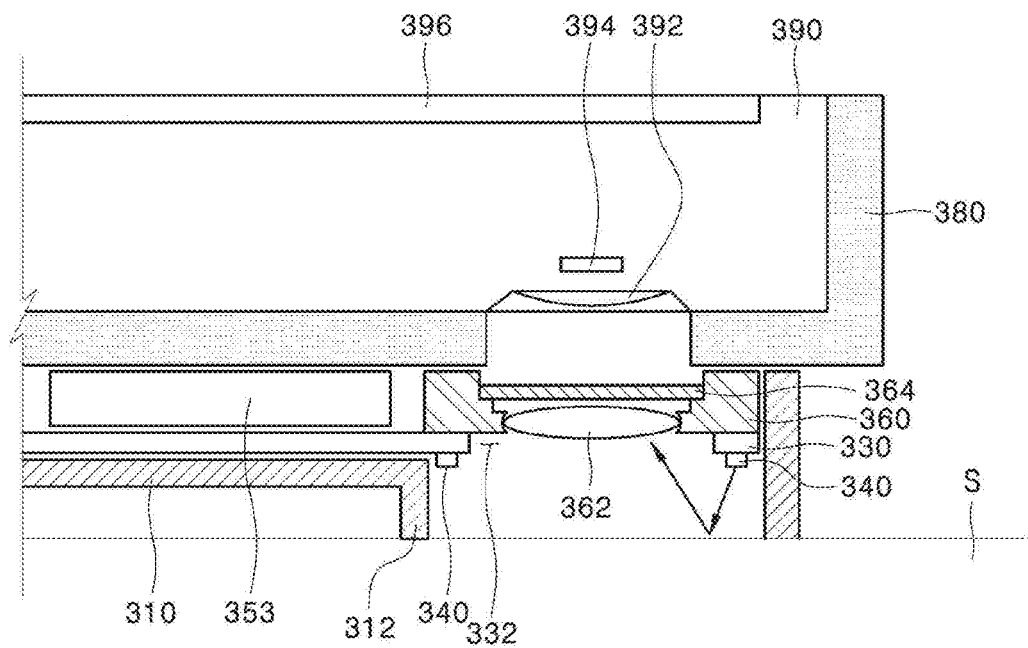
FIG. 34 is a cross-sectional view of the diagnosis device of FIG. 31.

Hereinafter, another example of the device for diagnosing acne vulgaris will be described. FIG. 31 is a perspective view showing another embodiment of a diagnosis device to which the method for diagnosing acne vulgaris according to the present disclosure is applicable, FIGS. 32 and 33 are exploded perspective views of the diagnosis device of FIG. 31 viewed from different directions, and FIG. 34 is a cross-sectional view of the diagnosis device of FIG. 31.

The device for diagnosing acne vulgaris according to the present disclosure may be implemented by the least components by using an image sensor 394, a central processing unit (CPU), a memory, or the like of a smart phone, which is a portable terminal carried by a person, together. As an example of the image sensor 394, the CCD is exemplified in the present disclosure. The image sensor 394 installed in the portable terminal may be configured as an array of a B sensor for detecting blue light, a G sensor for detecting green light, and an R sensor for detecting red light.

The device for diagnosing acne vulgaris according to the present disclosure may be implemented by the portable terminal 390 and a diagnosis module 301 to be described later.

The diagnosis module 301 includes a housing 310 for housing various components as its casing and a hollow cylindrical barrel 312 which is connected to the housing 310 and extends in a front direction in which it contacts skin. The housing 310 and the barrel 312 may be integrally made of synthetic resin. A height of the barrel may be about 24 mm, an outer diameter thereof may be about 29 mm, a height of the housing may be about 12 mm, and a width of the housing may be about 26 mm.

The inside of the casing is provided with a substrate 330 that is provided with a control circuit for controlling an operation of various components besides the LED. In particular, the substrate 330 fitted in the part of the barrel 312 of the casing has a disc shape corresponding to the barrel, a central part thereof is provided with a circular hole 332, and an annular substrate part is formed around the hole. Of course, the annular substrate portion housed in the barrel and the rectangular substrate housed in the housing are integrally formed. The annular substrate portion is provided with an LED 340 that irradiates blue light toward an outside of the opened barrel. The LED 340 is mounted on a circumference of the annular substrate at regular intervals and therefore does not generate directivity.

The LED 340 irradiates blue light having a peak wavelength of 407 nm to skin. At this time, the peak wavelength of the light emitted from the LED may be blue light to near-ultraviolet light existing in the range of 380 nm to 420 nm. This corresponds to the width of the spectrum corresponding to half of the maximum absorption rate in the absorption spectrum of the coproporphyrin 3 shown in FIG. 1. Therefore, if the peak wavelength of the light irradiated from at least the LED is within the range of 380 nm to 420 nm, the light energy absorption efficiency of the porphyrin existing in the skin can be secured to a considerable level.

The substrate 330 is provided with the control circuit for controlling the operation of the LED and a switch 351 for turning on and off the diagnosis module 301. In addition, the substrate 330 is electrically connected to a battery 353 which is housed in the housing 310 together. The substrate 330 is also provided with a power supply controller. The battery 353 is a secondary battery such as a lithium polymer battery, and may perform charging and discharging reversibly therein. The substrate 330 is provided with a charging terminal 352 for connecting an external power supply for charging the battery.

In addition, the substrate is provided with a Bluetooth chipset that transmits/receives a control signal to/from a main body of the portable terminal. A program for using the portable terminal as the device for diagnosing acne vulgaris may be installed in a portable terminal in the form of an application. For example, if a user presses a photographing button after driving the program, a control signal is transmitted to the control circuit of the substrate 330 through a Bluetooth protocol, so the LED 40 may be turned on. Then, the program may cause the image sensor 394 of the portable terminal 390 to photograph an image within a time period during which the LED 340 is turned on.

The control signal does not necessarily have to be transmitted in the Bluetooth manner. For example, a USB terminal on the portable terminal is connected to the charging terminal 352 on the substrate 330, and the charging terminal 352 is supplied with power from the USB terminal to be used for operating the LED or to charge the battery, and may be supplied with an LED control circuit from the USB type terminal and may transmit the LED control signal to the LED control circuit. In addition, it is possible to receive a control signal through an earphone or headphone connection terminal of the portable terminal. As described above, according to the present disclosure, the control signal may be transmitted/received between the portable terminal 390 and the diagnosis module 301 by applying various wired or wireless near field communication protocols.

Alternatively, the LED 340 may be driven by being simply turned on and off only by the switch 351. In other words, the user may control the LED by turning on the switch when he/she wants to diagnose the acne vulgaris and turning off the switch after the photographing ends.

Further, the diagnosis module 301 has a structure in which the battery 353 is omitted, and the charging terminal 352 may be used as a power supply terminal. For example, the USB terminal of the portable terminal 390 and the power supply terminal of the diagnosis module 301 which are described above may be connected in the wired manner to perform a supply of power in such a manner that the portable terminal 390 is supplied with power. Of course, as described above, it is possible to receive the LED control signal from the USB terminal and transmit the received LED control signal to the LED control circuit.

The substrate 330 is first fitted in the part of the barrel 312 and then a lens mounter 360 is fitted therein by an interference fit to be fixed. As the lens mounter 360 is fixed to the part of the barrel 312, the substrate 330 is also fixed together. A wide-angle lens 362 and a long pass filter 364 are each tightly fitted in the lens mounter 360 in order in order to be fixed. The lens mount 360 may be made of a synthetic resin material having elasticity to some extent to be tightly fitted easily.

The wide-angle lens 362 is to adjust a focal distance to the image sensor 394 of the portable terminal 390 even at the short distance of the housing. Therefore, the image of the skin may be focused on the image sensor 394 by the wide-angle lens 362 and the optical lens 392 of the portable terminal 390.

The long pass filter 364 passes only light having a wavelength of more than 500 nm. That is, the long pass filter 364 serves to exclude the blue light that has been irradiated to the skin and to pass the green light and pass light having a wavelength longer than that of the green light. Therefore, the RGB sensors of the image sensor 394 may react to the strong reflected light in the vicinity of 407 nm to prevent the corresponding pixel from becoming white.

The present disclosure exemplifies that the wide-angle lens 362 and the long-pass filter 364 are provided separately. However, in the actual manufacturing, the wide-angle lens 62 and the long-pass filter 64 may be integrally manufactured. For example, the wide-angle lens 362 is designed to be made of a PMMA resin having excellent light transmittance and is manufactured by injection molding, and may also perform the function of the long-pass filter by mixing a yellow-based pigment, which absorbs the wavelength of the first wavelength band, with a resin before the injection molding. According to the method, the number of assembled parts is reduced. Since the number of parts is reduced, it is possible to reduce the volume of the product and lower the manufacturing costs. That is, the lens has the shape of the wide-angle lens 362, and may also perform the function of the long-pass filter 364 by allowing a medium of the lens to absorb the light in the first wavelength band.

The housing 310 in which the above-described various components are built can be fixed to the portable terminal 390 by being fixed to the case 380. Of course, the present disclosure does not exclude other fixing methods.

If the housing 310 is fixed to the portable terminal 390, as shown in FIG. 34, the long pass filter 364, the wide-angle lens 362, and the circular hole 332 of the substrate are axis-aligned together with the image sensor 394 and the optical lens 392 of the portable terminal 390. At this time, if the portable terminal 390 or the case 380 thereof and the housing 310 of the diagnosis module 301 are provided with guide portions performing mutual guide so that the alignment is naturally made, the above-described alignment can be simply made.

As shown in FIG. 34, the tip part of the barrel 312 may photograph the skin while being in close contact with the skin S. That is, the barrel 312 contacts the skin, and thus the focal distance to the image sensor 394 is fixed to the distance between the image sensor 394 and the tip part of the barrel 312. In addition, the barrel 312 is made of an opaque substance, so that it is possible to prevent light from being irradiated to a space in the barrel from other light sources other than the LED 340. That is, the inside of the barrel satisfies a dark room condition in which there is no light source other than the LED 340.

Therefore, a skin contact type barrel 312 of the device for diagnosing skin of the present disclosure may make the scales of the images of the skin photographed by the image sensor 394 the same while satisfying the condition that lights other than the light irradiated from the LED emitting the light in the first wavelength range, for example, the blue light in the vicinity of 407 nm are not irradiated to the skin together.

Meanwhile, the diagnosis module 301 can be used while being attached to various portable terminals. However, when the diagnosis module 301 is used while being attached to different devices, the spectra of the sensitivities of the R, G, and B sensors of the image sensor installed in the corresponding device need to be grasped. That is, since the sensitivities of the R, G, and B sensors are different for each device, the R, G, and B values processed are different in the photographed images even if the same skin is photographed. Therefore, an expression f (R, G, B) reflecting the sensitivities of the R, G, and B sensors which are different for each device is required. However, manufacturers of the diagnosis module 301 may provide the expression as an application of the smart phone. That is, the applications implementing the image process to which the spectrum information of the sensitivities of the R, G, and B sensors grasped for each device is reflected are uploaded on an app store, and users download the uploaded applications, install the downloaded applications in the portable terminal, and then use the applications. As a result, the users may actively cope with various image sensors having different attributes.

Accordingly, the users may purchase only the diagnosis module 301 according to the present disclosure, install the purchased diagnosis module 301 in his/her own smart phone, and install the application, thereby implementing the diagnostic device. In addition, the diagnosis module 301 can be implemented by the least components described above, and therefore the price of the diagnosis module 301 may be lowered. Therefore, this makes it possible for users to use the diagnosis module conveniently at home.

Hereinafter, a method for diagnosing acne vulgaris of skin using the device will be described.

The user installs a program executing diagnosis of acne vulgaris in his/her own portable terminal 390. The barrel of the diagnosis module 301 and the part of the optical lens 392 of the portable terminal 390 are aligned, and the diagnosis module 301 is installed in the case 380 of the portable terminal 390.

The user turns on the switch 351 of the diagnosis module 301 and drives the program of the portable terminal 390 and connects the diagnosis module 301 and the portable terminal 390 via Bluetooth. Then, the program loads the characteristics of the image sensor 394 used for the corresponding model and the threshold for determination on whether the acne vulgaris occurs into the memory, according to the model of the corresponding portable terminal 390.

The user contacts the tip part of the barrel 312 to the skin at which acne vulgaris is to be diagnosed acne and presses the photographing button on the portable terminal 390. Then, the control signal is transmitted from the portable terminal 390 to the diagnosis module 301 via the Bluetooth protocol, and the LED control circuit and the power supply controller provided on the substrate 330 are operated to turn on the LED. The portable terminal 390 photographs the skin using the image sensor 394 while the LED is turned on. Then, the image photographed by the image sensor 394 detects light having a wavelength of 500 nm or more, and generates RGB values for each pixel.

The RGB values generated for each pixel are stored in the memory of the portable terminal. The central processing unit (CPU) of the portable terminal performs the image process on the photographed RGB values and compares values calculated by the RGB values of each pixel with the reference value to determine whether the corresponding pixel part is a part having a relation with acne vulgaris. Then, it is determined whether the area exceeds a predetermined reference.

The program of the portable terminal provides a mark informing a location where acne vulgaris has occurred or is highly likely to occur on the image photographed by the image sensor 394 and displays the mark on the display 396 of the portable terminal 390.

Then, the user may watch the display of the portable terminal, and determine that the area indicated by the light in the vicinity of 520 nm is a part where the inflammation will occur or the acne vulgaris has occurred. For reference, even the sebum in the pores is expressed by yellow or red, which is also noticeable.

In addition, if the number of outbreak (possible) points of acne vulgaris per unit area which becomes a reference is equal to or higher than a predetermined level, a method for informing a user of it in a manner such as sound or vibration or a visual manner through a display and prescribing or managing skin depending on a current skin condition may be proposed.

The diagnosis module 301 may simply diagnose acne vulgaris and may also be used in a therapy mode. At this time, a method of intensively irradiating blue light with the LED to a part determined to be acne vulgaris may be used. If porphyrin produced by P. acne absorbs light, the porphyrin has toxicity. By using the fact that the porphyrin absorbs energy from light in a spectrum range in the vicinity of 410 nm in response to photodynamic therapy (PDT) treatment which causes the toxicity to destroy the P. acne and sebaceous glands, the blue light stronger than when the skin is photographed for the skin diagnosis is irradiated around the acne vulgaris to obtain the treatment effect.

As a method for stronger irradiating blue light, a method of further increasing power supplied to LEDs to increase the amount of blue light irradiation per unit LED, a method of turning on all the plurality of LEDs, or a method of mixing these methods may be used. That is, when the skin is photographed for diagnosis, only some of the plurality of LEDs are turned on (of course, even in this case, the directivity is minimized by turning the LEDs at a location radially symmetrical with respect to the center). When the blue light is irradiated in the therapy mode, all the plurality of LEDs can be turned on (lit up) and the power supplied to each LED may be further increased.

In addition, the irradiated amount of the blue light for therapeutic purposes may be automatically adjusted in a program according to the size and number of acne vulgaris checked ii the diagnosis mode. As the method of adjusting an irradiated amount, a method of adjusting an irradiation time, a method of adjusting irradiation intensity, a method of mixing the methods, or the like may be used.

The switch 351 is simply configured in two stages. When the switch is at a first stage, the blue light is irradiated at an illuminance suitable for skin photographing, and when the switch is at a second stage, the blue light is irradiated at the illuminance suitable for the therapy mode.

The above-described combination of the portable terminal and the camera module or the diagnosis module can realize a small device, and can be easily used at home as well as places specializing in skin care. In addition, it is possible to perform the diagnosis by simply changing and installing only the camera module even for various skin diseases In particular, it is possible to greatly increase the use convenience by collecting and displaying the user data in real time.

According to the hyperspectral image measurement device and the calibration method thereof of the present disclosure, it is possible to obtain the reflectance map having the physical meaning and the high accuracy by providing the calibration method and the tool for converting the image acquired by using the hyperspectral measurement device into the reflectance map.

In addition, according to the embodiments of the present disclosure, it is possible to provide the device for diagnosing skin capable of easily replacing only the camera module without separately providing the diagnostic equipment for each skin disease to be diagnosed.

In addition, according to the present disclosure, it is possible to provide the device for diagnosing skin which can be used cheaply without taking up a large volume by combining the small camera module, which can be easily replaced according to the usage, with the personal portable terminal.

Further, according to the present disclosure, it is possible to diagnose the skin disease by oneself at home with the simple configuration alone.

According to the device for photographing and processing skin of the present disclosure, it is possible to minimize the distortion due to the image composition by obtaining the composed image as photographing the plurality of enlarged and photographed images at one time even if the plurality of enlarged and photographed images are composed.

Further, according to the device for photographing and processing skin of the present disclosure, it is possible to facilitate the skin diagnosis and treatment by easily and accurately matching the composed image with the actual skin.

According to the embodiments of the present disclosure, it is possible to prevent the skin trouble from occurring or the erythema, the scar or the like from being left due to the occurrence of acne vulgaris by diagnosing the locations, where the acne vulgaris is likely to occur, in advance.

Further, according to the present disclosure, it is possible for anyone to diagnose the acne vulgaris personally by providing the device capable of diagnosing the acne vulgaris with the simple configuration alone.

Further, according to the present disclosure, it is possible to further improve the user convenience by linking the diagnosis with the treatment.

In addition to the above-described effects, the detailed effect of the present disclosure will be described while describing the detailed matters to practice the present disclosure.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Only a few implementations and examples are described and other implementations, enhancements and variations can be made based on what is described and illustrated in this patent document.

What is claimed is:

1. A device for detecting an object, comprising:
a housing detachably connected to a portable terminal and including a first barrel portion that has a tip part contacting a periphery of the object and a second barrel portion that has a diameter smaller than the first barrel portion, wherein the first barrel portion includes a light emitting device configured to irradiate a first light having a first wavelength to a biological tissue in the object through the tip part;
a filter disposed in the second barrel portion to receive a reflected light from the biological tissue that includes a portion of the first light and a second light having a second wavelength and configured to block the portion of the first light and pass the second light; and
a sensor disposed to receive the second light from the filter and configured to detect the second light,
wherein the first wavelength is a wavelength at which a predetermined substance in the object has a high absorption rate,
wherein the second wavelength is a wavelength at which the predetermined substance fluoresces and has a longer wavelength than the first wavelength,
wherein the sensor includes at least one of a blue light sensing element, a green light sensing element, or a red light sensing element.

2. The device of claim 1, wherein the first light has a peak wavelength that is less than 420 nm.

3. The device of claim 1, wherein the filter is disposed to be closer to the sensor than the light emitting device.

4. The device of claim 1, wherein the sensor is an image senor.

5. The device of claim 1, further including a lens that is located on a path through which light emitting from the biological tissue is incident on the sensor.

6. The device of claim 5, wherein the lens is configured to block the portion of the first light and pass the second light.

7. The device of claim 6, wherein the lens includes PMMA.

8. A method for measuring an object, comprising:
irradiating, from a light emitting device, a first light having a first wavelength to an object without using another light source other than the first light to the object, wherein the object is configured to receive the first light and emit a light including a portion of the first light and emit a second light having a second wavelength longer than the first wavelength, wherein the light emitting device is included in a first barrel portion of a housing detachably connected to a portable terminal, the first barrel portion having a tip part contacting a periphery of the object and having a diameter greater than a second barrel portion of the housing;
applying a filtering operation to the light emitted from the object that includes a portion of the first light and a second light having a second wavelength longer than the first wavelength, the filtering operation configured to block the portion of the first light and pass the second light;
obtaining an image of a filtered light by using an image sensor; and
performing an image process operation on an obtained image based on optical information of the second wavelength.

9. The method of claim 8, wherein the first light has a peak wavelength that is less than 420 nm.

10. The method of claim 8, wherein the irradiating the first light is performed by a light emitting device and the filtering operation is performed by a filter that is disposed closer to the image sensor than the light emitting device.

11. The method of claim 8, wherein the first wavelength is a wavelength at which a predetermined substance in the object has a high absorption rate.

12. The method of claim 11, wherein the second wavelength is a wavelength at which the predetermined substance fluoresces and has a longer wavelength than the first wavelength.

* * * * *